United States Patent [19]

Cory, deceased et al.

[11] 4,077,842

[45] Mar. 7, 1978

[54] STABILIZED GLUCOSE ISOMERASE ENZYME CONCENTRATE

[76] Inventors: Robert Paul Cory, deceased, late of La Grange, Ill., by Cynthia S. Cory, executor, R.R. No. 6 P.O. Box 67, Danville, Ind. 46122

[21] Appl. No.: 668,380

[22] Filed: Mar. 19, 1976

[51] Int. Cl.² .................. C07G 7/02; C07G 7/028
[52] U.S. Cl. .................. 195/63; 195/31 F; 195/66 R; 195/68
[58] Field of Search .............. 195/31 F, 62, 66 R, 195/63, 68

[56] References Cited

U.S. PATENT DOCUMENTS

| | | | |
|---|---|---|---|
| 3,708,397 | 1/1973 | Sipos | 195/31 F |
| 3,715,276 | 2/1973 | Takasaki et al. | 195/31 F |
| 3,957,587 | 5/1976 | Armbruster et al. | 195/66 R |

*Primary Examiner*—David M. Nafe

[57] ABSTRACT

A stabilized glucose isomerase concentrate is prepared by contacting an aqueous mixture containing cell-free glucose isomerase and a water miscible organic solvent such as 2-propanol with a magnesium salt to form an enzyme-magnesium precipitate. The cell-free glucose isomerase may be prepared by mixing cells containing intracellular glucose isomerase with the water miscible organic solvent and digesting the cells with a lysozyme enzyme preparation. The stabilized concentrate contains magnesium and the water miscible organic solvent, and retains at least about 95% of its initial isomerase activity when stored at 26° C for up to 30 days and about 80% of its initial isomerase activity when stored at 18° C for up to one year.

27 Claims, No Drawings

STABILIZED GLUCOSE ISOMERASE ENZYME CONCENTRATE

BACKGROUND OF THE INVENTION a. Field of the Invention

This invention relates to a relatively pure and stable glucose isomerase enzyme concentrate in a water soluble form having a high specific activity and improved storage stability and the process for preparing the stabilized enzyme concentrate.

b. Description of the Prior Art

Transformation of dextrose to levulose, known as isomerization provides a product which in practice is a replacement for commercial invert sugar. Here one starts with dextrose, a monosaccharide sugar about 70% as sweet as sucrose or invert sugar, and converts up to one-half of it to a sugar about 140% as sweet as sucrose or invert sugar. It is this extra sweetness quality which interests the corn wet-milling industry in levulose-bearing corn syrup (commonly known today as high fructose corn syrups [HFCS]) and their manufacture.

Research on the enzymatic isomerization process began in 1955 and from this work came U.S. Pat. No. 2,950,228 to Marshall and the article by Marshall and Kooi in *Science,* 125, 648 (1957). From this point in time, the literature and patents literally exploded with descriptions of the work done by researchers spurred into activity by the initial work described by Marshall and Kooi.

One of the more significant papers was that of Drs. Sato and Tsumura of the Japanese Food Research Institute in their preliminary print of the Annual Meeting of the Agricultural Chemical Society of Japan held at Sapporo on July 20, 1964. In this 1964 preliminary print and its progeny appearing in Japanese Patent No. 17,640, published Oct. 7, 1966, Drs. Sato and Tsumura disclosed that several strains of microorganisms of the genus Streptomyces, when cultured on xylose, produce the enzyme, glucose isomerase, and reported also that it was effective in isomerizing glucose to fructose. In a subsequent development, another group of scientists working with Dr. Takasaki of the Japanese Fermentation Research Institute, which is an agency of the Ministry of International Trade and Industry (MITI), found that certain strains of microorganisms of the Streptomyces genus, which assimilate xylan (a polymer of xylose), can be cultivated on xylan with the production of glucose isomerase. The Takasaki et al. process and its progeny have been described in Japanese Patent No. 27,525 and in U.S. Pat. No. 3,616,221.

Manufacturers of high fructose corn syrup have found that the enzymatic isomerization of glucose should preferably be conducted on a continuous basis in order to economically produce a commercially acceptable high fructose corn syrup product. Generally, in such a process, a glucose syrup is contacted with a massive amount of a glucose isomerase enzyme preparation which has been located onto an inert substance, i.e., an immobilized glucose isomerase enzyme preparation. An essential aspect in such a process involves utilizing an immobilized glucose isomerase enzyme preparation which possesses a high concentration of isomerase activity per unit volume to thereby render the enzyme suitable in a continuous enzymatic isomerization process.

Glucose isomerase is generally produced intracellularly, i.e., the major portion of the glucose isomerase enzyme is located within and/or on the cell walls of the microorganisms from which it is produced. Some continuous isomerization processes contemplate the use of the whole cells containing the glucose isomerase. Such processes generally require special treatment of the cells to prevent extraction of the glucose isomerase from the cells so that the enzyme, in effect, is immobilized within the cells themselves, and/or special equipment to accommodate hydraulic problems encountered in driving the glucose-containing solution through the bed of cells containing the glucose isomerase enzyme. Examples of such processes which employ the whole cells containing glucose isomerase are described in U.S. Pat. Nos. 3,694,314; 3,753,858; 3,779,869; 3,817,832; 3,821,086; German OS 2,317,680; and German OS 2,345,186. These processes which employ the whole cells containing glucose isomerase suffer a number of disadvantages. These disadvantages include hydraulic problems, the formation of impurities due to the presence of non-isomerase enzymes, nucleic acids and other materials within the cell walls and longer contact times of the glucose solution with the cellular enzyme preparation (the latter of which under alkaline conditions will cause the formation of undesirable alkaline-catalyzed reaction products of fructose such as psicose and hydroxymethylfurfural [HMF]). The foregoing problems result in higher manufacturing costs due to the refining necessary to remove the impurities produced and/or the production of an inferior product.

In an effort to solve the problems encountered in using whole cells containing intracellular glucose isomerase, the prior art workers have proposed processes where the glucose isomerase is removed from the cells to place it in soluble form and thereafter immobilized on a water insoluble inert carrier. The immobilized enzyme is then suitable for use in continuously converting glucose to a high fructose corn syrup. Examples of such processes are described in U.S. Pat. Nos. 3,708,397; 3,788,945; 3,850,751; 3,868,304; Belgium Patent No. 819,859; U.S. Application No. 505,823 now U.S. Pat. No. 3,960,663, granted June 1, 1976 (Belgium Pat. No. 810,480).

While these processes which utilize cell-free immobilized glucose isomerase solve some of the problems encountered with the use of the whole cells, the processes require the step of solubilizing the glucose isomerase (i.e., removing the glucose isomerase from the whole cells). Processes for solubilizing the glucose isomerase are well-known. However, it is desirable to obtain cell-free and soluble glucose isomerase in a highly purified form which would possess a high level of isomerase activity per unit volume. The use of a highly purified and concentrated enzyme increases the efficiency with which the enzyme can be located on the insoluble carrier.

Processes for extracting and purifying glucose isomerase from cells of microorganisms in a concentrated and purified form have heretofore involved costly and complicated procedures, only suitable in small scale laboratory operations.

One such laboratory procedure for extracting and purifying solubilized glucose isomerase has been described by Danno et al. in Agr. Biol. Chem., Vol. 31, pp. 284–292 (1967). Danno et al. described a process for purifying glucose isomerase derived from Bacillus coagulans strain HN-68 by subjecting ethylene diamine tetraacetic acid (EDTA) treated cells to lysozyme to prepare a cell-free extract followed by treatment of the cell-free extract with manganese sulfate to produce a precipitate of unwanted materials. The supernatant was repeatedly treated with ammonium sulfate to precipitate a proteinaceous glucose isomerase fraction which was further purified by dialysis and chromatography on DEAE-Sephadex A-50 (a registered trademark). A 60-fold increase in concentration was reported.

Another laboratory procedure for purifying glucose isomerase has been described by Takasaki et al., (Agri. Biol. Chem., Vol. 33, pp. 1527–1534 [1969] and "Fermentation Advances", Edited by D. Perlman, pp. 561–589 Academic Press, Inc., New York, New York [1969]). Takasaki et al. disclosed that intracellular glucose isomerase derived from Streptomyces albus could be released from the cells by treatment with the cationic surface active agent, cetyl pyridinum chloride and then fractionated by sequential treatment of the cell-free extract with acetone, dialysis treatment, followed by DEAE-cellulose and DEAE-Sephadex column chromotography and further dialysis. The purified cell-free extract was further purified by dialysis in a solution containing 0.005 M magnesium sulfate and 0.0002 M $CoCl_2$. Acetone was gradually added to the resulting solution to a concentration of 40, 45 and finally 50% to crystallize the glucose isomerase enzyme. This process is too complicated and time-consuming to be applicable on a large scale operation.

U.S. Pat. No. 3,708,397 to Sipos described a process of extracting glucose isomerase from EDTA treated cells of the microorganism Streptomyces phaeochromogenes grown on wheat bran followed by treatment with a solution containing lysozyme, toluene, magnesium chloride, buffer and water. The lysed slurry was treated with magnesium chloride and ultimately, the enzyme was precipitated by the gradual addition of cold acetone. This enzyme precipitate was dissolved in water and immobilized on DEAE-cellulose for use as a biocatalyst to convert glucose to a high fructose corn syrup.

In U.S. Pat. No. 3,788,945 to Thompson et al., there has been described a process wherein intracellular glucose isomerase derived from Streptomyces sp ATCC 21,175 grown on xylose and xylan hydrolysate was treated with a cationic detergent (Arquad 18–50), followed by treatment with DEAE-cellulose to remove non-isomerase material. The filtrate containing glucose isomerase was then immobilized on DEAE-cellulose or a synthetic anion exchange resin to prepare the biocatalyst to continuously convert glucose to a high fructose corn syrup.

In U.S. Pat. Nos. 3,847,740 and 3,847,741 to Heady et al., there has been described a process for treating cells containing intracellular glucose isomerase with a small amount of the surfactant, Tween 80, (a registered trademark) in a buffered glycine solution. After thorough mixing, the cellular debris was removed and a filtrate containing 17.5 U/ml of isomerase activity was obtained.

U.S. Pat. No. 3,847,740 has provided a process for immobilizing purified glucose isomerase preparations on a basic magnesium carbonate carrier and U.S. Pat. Nos. 3,850,751 and 3,868,304 have provided processes for immobilizing glucose isomerase preparations on controlled porous carriers of alumina. The use of these immobilized enzyme preparations provide superior processes for producing high fructose corn syrups, but require a highly purified and concentrated glucose isomerase for their efficient and economical commercialization.

In spite of the processes previously described, there is still a need for an economically feasible process, adaptable for large scale operation, for producing a substantially soluble and purified glucose isomerase preparation have a high level of activity per unit volume and a high level of stability suitable for binding to water insoluble carriers for use in continuous processes in the manufacture of high fructose corn syrups, but also useful per se, and in other immobilization processes.

SUMMARY OF THE INVENTION

One aspect of the present invention is directed to a substantially water soluble stabilized enzyme concentrate comprising an enzyme concentrate of (1) a cell-free glucose isomerase enzyme which is substantially free of nucleic acids and (2) a substantially water soluble magnesium salt, said enzyme concentrate being characterized as having: (a) a protein content ranging from about 50 to about 80%, by weight, dry basis; (b) a $Mg^{++}$ content ranging from about 3 to about 45 mg. of $Mg^{++}$ per ml. of enzyme concentrate; (c) a $Mg^{++}$/protein ratio ranging from about 0.02 to about 0.75; (d) a specific isomerase activity of at least about 10 IGIU/mg. of protein; and (e) a stability such that it retains up to 95% of its initial isomerase activity when stored at room temperature (26° C.) for up to 30 days and up to 80±10% of its initial isomerase activity when stored at 18° C. for up to 12 months.

The enzyme concentrate preferably contains a water miscible organic solvent such as 2-propanol in an amount ranging from about 5 to about 25%, by weight, and possesses an isomerase activity of at least about 5,000 IGIU/gram, dry basis and more preferably at least about 8,000 IGIU/gram, dry basis.

Another aspect of the invention is directed to the method of concentration, purification and stabilization of the glucose isomerase enzyme.

The stabilized enzyme concentrate of the present invention is prepared by contacting an aqueous mixture containing cell-free glucose isomerase enzyme and a water miscible organic solvent with a small, but effective amount of a substantially water soluble magnesium salt to effect precipitation of the glucose isomerase enzyme and magnesium salt. This treatment with the magnesium salt causes the formation of a glucose isomerase enzyme-magnesium precipitate which is subsequently recovered by conventional techniques such as by centrifugation. The recovered stabilized enzyme concentrate (which is in the form of a thick slurry) is preferably diluted with a small amount of water to facilitate its sorption onto water insoluble carriers to form a highly stable, immobilized glucose isomerase biocatalyst having a high level of isomerase activity per unit volume of carrier. The concentration, purification and stabilization process produces better than a 70-fold increase in concentration of the enzyme from its original fermentation broth, and preferably better than a 100-fold increase in concentration. The enzyme concentrate is also 10–15 times more pure than the original enzyme.

Another aspect of the present invention involves treating a mixture of cell-free glucose isomerase enzyme with a water miscible organic solvent, in an amount sufficient to precipitate a substantial amount of the nucleic acids, but less than that amount which precipitates the enzyme. This intermediate concentrated and purified enzyme is useful, per se, although lacking in stability and concentration compared to the magnesium treated enzyme concentrate of the present invention.

DEFINITIONS

Because of the plethora of terms that are in common use in the art, a few definitions are given to simplify the present application and permit it to be more concise.

D.E.

The term "D.E." is an abbreviation of "dextrose equivalent" and these terms are used interchangeably to refer to the reducing sugar content of a material, calculated as dextrose, and expressed as percent of total solids.

Starch Hydrolysate

The term "starch hydrolysate" is used in a general way to refer to a syrup or dry product that is made by the hydrolysis of starch. Such a product may be made by acid or enzymatic hydrolysis or by a combination of acid and enzymatic hydrolysis. A preferred type of starch hydrolyzate for use for isomerization in accordance with the present invention is produced by acid or enzyme thinning to a D.E. of 10 or less, followed by enzymatic saccharification to a D.E. above 90, preferably above 95. The term "dextrose" is commonly reserved, in commercial usage, for the refined crystalline sugar (a monosaccharide) that is recovered from a highly converted starch hydrolyzate. The term "glucose" will be used herein both in its usual commercial sense and also to embrace the monosaccharide dextrose in any form, in solution or dry, as a constituent of a starch hydrolyzate syrup or syrup solids, or in refined crystalline form.

FRUCTOSE AND LEVULOSE

The terms "fructose" and "levulose" are generally employed interchangeably in the art to refer to the levo rotary isomer of glucose that is sweeter than dextrose. This isomer is found naturally in honey and in invert sugar along with glucose, and it is valuable because of its sweetness. The term "fructose" will be used to refer to this monosaccharide.

GLUCOSE ISOMERASE ENZYME

"Glucose isomerase enzyme" is the enzyme or enzyme preparation that is capable of isomerizing xylose to xylulose and glucose to fructose. The predominant activity of this enzyme is in the conversion of xylose to xylulose and the term xylose isomerase is the most accurate scientific name (EC 5.3.1.5). It has also been referred to in the art as dextrose isomerase, xylose (dextrose) isomerase and glucose isomerase. The term most commonly used is "glucose isomerase" and that term will be used herein for the sake of simplicity and understanding.

Units

In this application, all parts and percentages are by weight, and on an "as is" basis, unless expressly stated to be otherwise.

IGIU

The term "IGIU" is an abbreviation for International Glucose Isomerase Unit. One IGIU is the amount of glucose isomerase enzyme that will form one micromole of fructose per minute in an 0.8 molar solution of glucose at pH 7.5 and at 60° C., using the assay procedure described below under the heading "Assay of Isomerase Activity".

ASSAY OF ISOMERASE ACTIVITY

The assay procedure involves making a spectrophotometic determination of the ketose produced from a glucose solution under a standardized set of conditions.

A stock solution is made up in the following manner:

| Stock Solution for Assay | |
|---|---|
| Component | Amount |
| 0.1 M $MgSO_4 \cdot 7H_2O$ | 1 ml |
| 0.01 M $CoCl_2 \cdot 6H_2O$ | 1 ml |
| 1.0 M Phosphate buffer, pH 7.5 | 0.5 ml |
| Anhydrous D-glucose | 1.44 g. |
| Distilled water | To make up a total volume of 7.5 ml. |

The enzyme preparation to be assayed is first diluted to contain from 1 to 6 IGIU/ml.

An enzymatic isomerization is conducted by adding 1 ml of the enzyme preparation to 3 ml of the stock solution, and incubating for 30 minutes at 60° C. At the end of the incubation period, a 1 ml aliquot is taken and quenched in a 9 ml volume of 0.5 N perchloric acid. The quenched aliquot is then diluted to a total volume of 250 ml. As a control, for comparative purposes, a glucose blank is also run by substituting 1 ml of water for 1 ml of the enzyme preparation in solution form, at the beginning of the incubation period. The ketose is then determined by a cysteine-sulfuric acid method. For the purposes of this assay, one IGIU is defined as the amount of enzyme activity that is required to produce one micromole of fructose per minute under the isomerization conditions described above.

LYSOZYME ENZYME PREPARATION

Lysozyme enzyme (EC 3.2.1.17) is an enzyme which hydrolyzes beta-1,4-links between N-acetyl-muramic acid (or 2-acetamido-2-deoxy-D-glucose) and 2-acetamido-2-deoxy-D-glucose residues in a mucopolysaccharide, mucopolypeptide or in chitin. Lysozyme is generally produced from egg whites. It catalyzes the hydrolysis (lysis) of the cell walls of many microorganisms.

DESCRIPTION OF THE PREFERRED EMBODIMENTS

The substantially water soluble stabilized enzyme concentrates of the present invention are enzyme concentrates of (1) a cell-free glucose isomerase enzyme which is substantially free of nucleic acids, and (2) a substantially water soluble magnesium salt. The enzyme concentrates are characterized as having: (a) a protein content ranging from about 50 to about 80%, preferably 60 to about 75%, by weight, dry basis; (b) a $Mg^{++}$ content ranging from about 3 to about 45, preferably 5 to about 25 mg. of $Mg^{++}$ per milliliter of enzyme concentrate; (c) a $Mg^{++}$/protein ratio ranging from about 0.02 to about 0.75, preferably from about 0.03 to about 0.5; (d) a specific isomerase activity of at least about 10 IGIU/mg. of protein, preferably at least about 12 IGIU/mg. of protein and most preferably at least about 15 IGIU/mg. of protein; (e) a water miscible solvent present in an amount ranging from about 5 to 25%, by weight and preferably 10 to about 20%, by weight; and (f) a stability such that up to 95% of the initial isomerase activity is retained when stored at 26° C. for up to 30 days and up to 80±10% of the initial isomerase activity is retained when stored at 18° C. for up to one (1) year. The stabilized enzyme concentrates possess at least about 5,000 IGIU/gram, dry basis, preferably at least about 8,000 IGIU/gram, dry basis and most preferably at least about 10,000 IGIU/gram, dry basis.

The stabilized enzyme concentrates of the present invention, due to the process by which they are prepared in accordance with one aspect of the invention are substantially free of nucleic acids such as ribonucleic acid (RNA) and deoxyribonucleic acid (DNA).

The stabilized enzyme concentrates, when in liquid form, will generally possess a magnesium molarity ranging from about 0.1 to about 2 molar, calculated as magnesium, and preferably an amount ranging from about 0.2 to about 1.0 molar, calculated as magnesium.

While the enzyme concentrates are generally in liquid form, they may be dried to a solid or diluted with water and other materials. The preferred enzyme concentrates possess a moisture content in the range from about 50 to 80%, and most preferably in the range from about 55 to about 70%. The dry substance of the enzyme concentrates is preferably in the range from about 5 to about 30%, and more preferably in the range from about 20 to about 30%, by weight.

The most preferred stabilized enzyme concentrates of the present invention are free from any added cobalt, and the glucose isomerase enzyme is preferably derived from a microorganism of the Streptomyces genus, most preferably a microorganism which is a member selected from the group consisting of *Streptomyces olivochromogenes* ATCC No. 21,713, ATCC No. 21,714, ATCC No. 21,715, variants and sub-mutants thereof.

The stabilized enzyme concentrates of the present invention are preferably prepared by a process comprising:

a. treating an aqueous mixture containing cell-free glucose isomerase and a water miscible organic solvent with a substantially water soluble magnesium salt in an amount sufficient to provide the mixture with from about 0.02 molar to about 0.3 molar with respect to the magnesium salt based on the total volume of mixture to provide a stabilized enzyme concentrate comprising an enzyme-magnesium precipitate in the mixture, and b. recovering the stabilized enzyme concentrate containing a glucose isomerase enzyme which contains magnesium in an amount from about 0.1 to about 2 molar measured as $Mg^{++}$, water and the water miscible organic solvent.

The stabilized enzyme concentrate is preferably prepared by first subjecting cells containing intracellular glucose isomerase to treatment with a water miscible organic solvent and a lytic enzyme preparation such as a lysozyme enzyme preparation derived from egg whites for a sufficient amount of time to digest the cellular material and allow the glucose isomerase enzyme to be released into solution from the cells. The cellular debris and nucleic acids are then removed as by centrifugation and a solution comprising the cell-free glucose isomerase enzyme, the water miscible organic solvent and water remains.

The water miscible organic solvent used in the practice of the invention is preferably an organic liquid or mixture thereof having a water solubility of at least 30%, and preferably at least about 40% in water at room temperature. The water miscible organic solvent should be one which decreases the solubility of proteins and nucleic acids in aqueous solutions. Typical water miscible organic solvents suited for the present invention include methanol, ethanol, propanol, 2-propanol, t-butyl alcohol, acetone, and p-dioxane. The preferred water miscible organic solvent is 2-propanol.

The amount of water miscible organic solvent employed in the process of the invention will generally be an amount sufficient to provide the aqueous mixture at least about 30%, by weight, and preferably at least about 40%, by weight with respect to the water miscible organic solvent. However, the amount of water miscible organic solvent employed should be such that a substantial portion of the non-isomerase proteinaceous materials and nucleic acids such as ribonucleic acid (RNA) and deoxyribonucleic acid (DNA) precipitate from the solution prior to salt addition. The maximum level of the solvent, of course, will vary from one solvent to another. Generally speaking, 60%, by weight is the upper limit for most solvents contemplated by this invention. Typically, when 2-propanol is employed as the water miscible organic solvent, the aqueous solution of the cell-free glucose isomerase will contain about 40-45%, by weight of the solvent and preferably 42±1%, by weight 2-propanol.

The water miscible organic solvent tends to serve several distinct purposes, namely, it acts as a preservative for the enzyme during processing (and during storage if the solvent is not completely removed) and it decreases the solubility of the enzyme during the salt addition. It also acts to precipitate the nucleic acids and other non-isomerase proteinaceous materials from the solubilized glucose isomerase prior to the treatment with the substantially water soluble magnesium salts. Thus, a concentrated and higher purity isomerase is obtainable by the use of the water miscible organic solvent alone.

The manner of when and how the water miscible organic solvent is added to the solution containing cell-free glucose isomerase may vary. One procedure involves first treating a centrifuged paste of cells which contain intracellular glucose isomerase with a portion of the water miscible solvent to be used. The aqueous slurry of cells and solvent are then treated in a manner to release the isomerase from the cells. Such treatments include sonication, freeze-thaw procedures, or treatment with surfactants, and/or lytic enzyme preparations, such as lysozyme. The use of lytic enzymes is preferred from the standpoint of large-scale operations. After the enzyme has been released from the cells, an additional amount of the solvent is added to the solution up to the point where nucleic acids and extraneous proteins precipitate but the isomerase enzyme remains soluble. The cellular debris and precipitated extraneous materials are then removed. At this point the substantially water soluble magnesium salt is added to form a precipitate of the stabilized enzyme concentrate.

Another technique of employing the solvent involves adding substantially all of the pre-determined amount of solvent to the cellular paste of glucose isomerase. By this technique, the cellular paste obtained by centrifuging a broth of cells containing intracellular glucose isomerase is treated with the full amount of the water miscible organic solvent along with water to provide a solvent/water slurry of cells. The slurry containing water miscible organic solvent is treated to release the glucose isomerase enzyme from the cells. Following removal of the insoluble material which includes the cellular debris and nucleic acids, the clarified solution containing cell-free glucose isomerase, solvent and water is treated with the substantially water soluble magnesium salt to precipitate the stabilized enzyme concentrate.

The temperature and pH conditions during the processing should be such that the enzyme is not inactivated. Generally, the pH should be in the range from about 6 to 9 and preferably from 7 to 7.5 during each step of the process. The temperature can be in the range from about 5° C. to about 55° C., preferably in the range of from 15° C. to about 35° C., most preferably 25° C. to 30° C.

The substantially water soluble magnesium salt used in the practice of the invention is preferably one which is substantially water soluble at a concentration in the range from about 0.02 molar to about 2 molar at room temperature. Typical useful magnesium salts include magnesium chloride, magnesium bromide, magnesium nitrate, magnesium sulfate heptahydrate, magnesium acetate and magnesium lactate. Magnesium sulfate heptahydrate and magnesium chloride are preferred and magnesium sulfate heptahydrate is most preferred. (Wherever magnesium sulfate is referred to in this description, it is to the heptahydrate form).

The amount of the substantially water soluble magnesium salt employed in the process of the present invention should be at least enough to provide the liquid containing the aqueous slurry of the water miscible organic solvent and the cell-free glucose isomerase enzyme at least about 0.02 molar with respect to magnesium ion. The upper limitation on the concentration of the magnesium salt will vary depending on the salt employed. The magnesium salt should not be added to the extent that a total "salting out" effect or salt-water phase separation occurs. Generally speaking, the maximum amount of the magnesium salt in the solution is about 0.3 molar. Preferably, the magnesium salt concentration in the solution will be in the range from about 0.02 molar to about 0.2 molar based on magnesium ion content. Best results have been found by adding the magnesium salt in an amount to provide the solution about 0.05 with respect to magnesium ion.

The intracellular glucose isomerase enzyme from which the stabilized enzyme concentrates are prepared may be derived from any suitable microorganism capable of producing the glucose isomerase enzyme. Examples of suitable microorganisms include those derived from the genera *Streptomyces, Bacillus, Arthrobacter, Actinoplanes, Curtobacterium* and others. Specific microorganisms which may be used in the preparation of the intracellular glucose isomerase enzyme starting material include *Streptomyces fradiae, Streptomyces phaeochromogenes, Streptomyces albus* ATCC No. 21,132; *Streptomyces wedmorensis* ATCC No. 21,230, the latter two are mentioned in U.S. Pat. No. 3,616,221; *Streptomyces rubiginosus* ATCC No. 21,175 and ATCC No. 21,176 mentioned in U.S. Pat. Nos. 3,666,628 and 3,788,945; *Streptomyces olivaceus* NRRL 3583 as mentioned in U.S. Pat. No. 3,625,828; and *Streptomyces olivaceus* NNRL 3916 as mentioned in British Patent No. 1,376,787; *Streptomyces olivochromogenes* ATCC No. 21,114 as mentioned in U.S. Pat. Nos. 3,622,463 and 3,770,589; and *Streptomyces olivochromogenes* ATCC Nos. 21,713, 21,714 and 21,715 as mentioned in U.S. Pat. Nos. 3,813,318 and 3,957,587; *Streptomyces venezuelae* ATCC No. 21,113 as mentioned in U.S. Pat. No. 3,622,463; *Streptomyces glaucescens* as mentioned in British Patent No. 1,410,579; *Streptomyces violaceoniger* as mentioned in German OS 2,417,642; *Arthrobacter nov sp* NRRL B-3724, NRRL B-3725, NRRL B-3726, NRRL B-3727 and NRRL B-3728 as disclosed in U.S. Pat. No. 3,645,848; *Bacillus stearothermophilus* ATCC No. 21,365, NRRL B-3680, NRRL B-3681, and NRRL B-3682 as mentioned in U.S. Pat. No. 3,826,714; *Lactobacillus brevis; Bacillus coagulans,* NRRL Nos. 5649 – 5666, and particularly NRRL No. 5650 as mentioned in German OS 2,400,323; *Actinoplanes missouriensis* NRRL B-3342, *Actinoplanes philippinesis* ATCC No. 12,427, *Actinoplanes armeniacus* ATCC No. 15,676 and *Actinoplanes sp* ATCC 23,342 as mentioned in U.S. Pat. No. 3,834,988; *Aerobacter levanicum* NRRL B-1678 as mentioned in U.S. Pat. No. 3,813,320; and *Nocardia asteroides* ATCC No. 21,943, *Nocardia dassonvillei* ATCC No. 21,944, *Micromonospora coerula* ATCC No. 21,945, *Microbispora rosea* ATCC No. 21,946 and *Microellobospora flavea* ATCC No. 21,947 as mentioned in U.S. Pat. No. 3,829,362; and *Curtobacterium* as mentioned in Japanese Sho 50/132176 (1975).

The most preferred glucose isomerase enzymes useful as starting materials in the practice of the present invention are those derived from *Streptomyces olivochromogenes* ATCC No. 21,713, ATCC No. 21,714 and ATCC No. 21,715, (the latter of which is a single colony isolate of ATCC No. 21,713) mentioned in U.S. Pat. No. 3,813,318 and U.S. Application Ser. No. 589,115, filed June 23, 1975 now U.S. Pat. No. 3,957,587, granted May 18, 1975, particularly when prepared by the process described and claimed in U.S. Pat. No. 3,770,589.

The intracellular glucose isomerase enzyme is preferably produced by growing a glucose isomerase producing microorganism such as the strains hereinabove mentioned in a suitable culture medium in a suitable carbon source and other appropriate nutrients and allowing the enzyme to be formed.

For example, an inoculum containing a glucose isomerase producing strain is prepared, e.g., on an agar slant and it is used to inoculate a suitable culture medium. Then the organism is allowed to grow and produce the intracellular glucose isomerase enzyme. The incubation period may vary over a wide range depending upon the particular microorganism used and upon the culture medium, preferably it is between 4 and 48 hours. An aliquot or the entire culture is then used to inoculate a suitable culture medium in one or more development stages whereupon the inoculum from the final development stages is used to inoculate a suitable medium in a fermentor.

The broth containing the intracellular glucose isomerase enzyme can be recovered and concentrated by any suitable means such as by centrifugation and/or filtration. The cell paste comprising the cells containing intracellular glucose isomerase is then in a suitable form to be processed in accordance with the process of the present invention.

The following examples serve to more fully describe the manner of making and using the above-described invention, as well as to set forth the best modes contemplated for carrying out various aspects of the invention. It is to be understood that these examples in no way serve to limit the true scope of this invention, but rather, are presented for illustrative purposes only. It will be understood that all proportions are in parts by weight, unless otherwise indicated. Glucose isomerase activity was determined by the procedure described hereinabove under the heading "Assay of Isomerase Activity" and referred to as IGIU as defined hereinabove.

EXAMPLE 1

(a) Preparation of Intracellular Glucose Isomerase

The intracellular glucose isomerase enzyme preparation used to prepare the stabilized enzyme concentrate was produced in four(4) inoculum development stages starting with 1-liter shake flasks and leading up to 1,000-gallon (3,785.4 liters) seed tanks and culminating in the final 20,000 gallon (75,708 liters) fermentors. Each successive development stage and the 20,000-gallon fermentors were inoculated with a volume of seed equal to 5% of the volume of the inoculated vessel. The composition of the media for the seed development and the operating procedures are given in Table I. The media for each of the steps was sterilized for 30 minutes at 120° C. The time for inoculation development was 48 hours for the first stage, 24 hours for the second stage, 22 hours for the third stage and 15-17 hours for the fourth stage. In the first stage, cells from a sporulated mutant strain of a microogranism identified as *Streptomyces olivochromogenes* ATCC No. 21,715 (a single colony isolate of ATCC No. 21,713, as disclosed in U.S. Pat. Nos. 3,813,318 and 3,957,587, the disclosures of which are incorporated herein by reference) were added to the culture media. The four inoculum development stages were conducted at a temperature of 28° C and at a pH of 7.0 (adjusted prior to sterilization with 10 N sodium hydroxide).

TABLE I

| Development Stage | Medium | Weight, % | Weight | | Operating Volume |
|---|---|---|---|---|---|
| 1st Stage (Three 1-liter Shake Flasks) | Corn steep liquor, Code E801 | 3.6 | 7.2 | g. | 200 ml. |
| | 15 D.E. Corn syrup solids | 1.0 | 2.0 | g. | 200 ml. |
| | Magnesium sulfate . 7H$_2$O | 0.05 | 0.7 | g. | 200 ml. |
| | Antifoam, HODAG 2000 (Polypropylene Glycol) | — | 0.07 | ml. | 200 ml. |
| 2nd Stage (14-liter Bench Fementor) | Corn steep liquor, Code E801 | 3.6 | 271 | g. | 9-liter |
| | 15 D.E. Corn Syrup solids | 2.0 | 180 | g. | 9-liter |
| | Magnesium sulfate . 7H$_2$O | 0.05 | 4.5 | g. | 9-liter |
| | Antifoam, HODAG 2000 (Polypropylene Glycol) | — | 1.3 | ml. | 9-liter |
| 3rd Stage (50-gallon Inoculum tank) | Corn steep liquor, Code E801 | 3.6 | 5.44 | kg. | 40-gallon |
| | Starch, Code 3005 | 2.0 | 3.04 | kg. | 40-gallon |
| | Magnesium sulfate . 7H$_2$O | 0.05 | 75.75 | g. | 40-gallon |
| | Antifoam, HODAG 2000 (Polypropylene Glycol) | — | 51 | ml. | 40-gallon |
| 4th Stage (1000-gallon Seed tank) | Corn steep liquor, Code E801 | 3.6 | 108.86 | kg. | 800-gallon |
| | Dextrose, Code 2001 | 2.0 | 60.33 | kg. | 800-gallon |
| | Magnesium sulfate . 7H$_2$O | 0.05 | 1.497 | kg. | 800-gallon |
| | Antifoam, HODAG 2000 (Polypropylene Glycol) | — | 1-liter | | 800-gallon |

During the second, third and fourth inoculum development stages, the flasks and tanks were subjected to aeration and agitation during the fermentations.

The final fermentations were conducted in 20,000-gallon fermentors. The medium ingredients, less xylose and dextrose, were batched up in 14,000 gallons (52,996 liters) of condensate. After makeup, the medium was heated to about 140° F (60° C) and the pH was adjusted to 5.6–5.8 with 16° Baume soda ash. The broth was heated prior to adjustment to drive off the carbon dioxide which evolved upon addition of the soda ash. After the pH of the medium was adjusted, the antifoam was added and the fermentor and contents were sterilized for 30 minutes at 120° C. After sterilization, the temperature of the medium was reduced to 60° C. The sugars, xylose and dextrose, were batched up in 400 gallons (1,514 liters) of condensate in the 1000-gallon seed tank. The sugar solution was sterilized for 30 minutes at 120° C and after cool-down, the sugar solution was transferred to the 20,000 gallon fermentors using an inoculum hose. After sugar addition, the temperature of the fermentor was stabilized at the operating value of 32° C and then the fermentor was inoculated with the seed culture. Beginning at 20 hours after inoculation, samples of the fermentor broth were taken every 2 hours and analyzed for isomerase activity, cell weight, reducing sugars and total carbohydrates. The fermentation was considered to be complete when the production of isomerase enzyme had peaked. During the fermentation, pH was controlled so it did not fall below 5.4–5.6 by automatic or manual additions of ammonia gas through the fermentor air sparge lines under pre-sterilized conditions. The medium makeup and the operating parameters for the fermentation in the 20,000 gallon fermentor which have been described in U.S. Pat. Nos. 3,770,589, and 3,813,318 are presented in detail in Table II.

TABLE II

Medium Make-up for 20,000 Gallon Fermentors
Make-up Volume - 17,000 gallons (64,352 liters)

| Medium Contents | Weight, % | Weight, kg. |
|---|---|---|
| Corn steep liquor, code E801 | 4.0 | 2,600.44 |
| Starch, Code 3005 | 2.5 | 1,625.22 |
| Dextrose, Code 2001 | 0.2 | 130.18 |
| Xylose | 1.0 | 649.99 |
| Glycine | 0.1 | 64.86 |
| Ammonium Nitrate | 0.2 | 130.18 |
| Magnesium Sulfate | 0.05 | 32.66 |
| Antifoam, HODAG 2000 (Polypropylene Glycol) | | 20.82–22.71 liters |
| Sodium Bicarbonate (Added prior to sterilization to adjust pH to 5.8–6.0) | | |
| Final Volume = 18,000 gallons (68,137.4 liters) | | |
| Operating Temperature = 31° C. | | |

No cobalt was added during any stage of the fermentation or during the inoculum development stages.

The intracellular glucose isomerase enzyme recovered from the broth had 19.5 IGIU/ml. A 2,340 gallon (8857.9 liters) portion of the broth was taken for use in the preparation of the stabilized glucose isomerase enzyme concentrate. Another portion of the broth was recovered in the form of whole cells using Mg(OH)$_2$, Sil-Flo 332 filter aid and 2-propanol. The latter recovered whole cells were then used to enzymatically convert glucose to fructose in a batch convertor.

b. Preparation of stabilized glucose isomerase enzyme concentrate.

A 2,340 gallon (8,857.9 liters) portion of the intracellular glucose isomerase enzyme broth from the 20,000 gallon fermentator as prepared above having 19.5 IGIU/ml for a total of 173 × 10$^6$ IGIU) was processed through a DeLaval BRPX-207 solids ejecting centrifuge. The machine was supplied at a rate of 5 gallons per minute with a 2-minute shoot cycle. Wash and prime water were added for one second just prior to, and following, the bowl shoot. The cell paste comprising 2,023 pounds (917.6 kg) having 187 IGIU/g from the shoot discharge of the machine was put into a 225-gallon round bottom tank with 20 gallons of water. When 650–700 pounds (294.8–317.5 kg) of cell paste were collected, the cell paste was treated with 8 grams of a lysozyme enzyme preparation (a 2X crystalline freeze-dried powder prepared by Miles-Seravac derived from egg whites having an activity of 23,300 units per milligram of material) to commence digestion of the cell walls releasing the intracellular glucose isomerase enzyme in a soluble form. A solution of 2-propanol (85% by volume) and water was added to the cell paste on a 5.6 gallons (21.2 liters) of solution per 100 pounds (45.36 kg) paste basis. An additional 11 gallons (41.64 liters) of the 2-propanol - water solution was added to the mixture to bring the alcohol content of the liquid to 30% by volume. The paste-2-propanol-water mixture was then pumped to a 1000-gallon (3,785.4 liter) digestion tank, and digestion was allowed to continue for 24 hours. The temperature of the liquid in the digestion tank was held at about 79° F ± 2° (26° C). After 24-hours of digestion, the mixture was modified by the addition of 85% 2-propanol to bring the 2-propanol content to 52% by volume at which point the nucleic acids such as ribonucleic acid and deoxyribonucleic acid (DNA) are substantially insoluble and the proteinaceous enzyme material is soluble. A rotary vacuum precoat filter was precoated with 200 pounds (90.7 kg) of Dicalite 4200 filter aid. When the precoat was established, 2-propanol was added to the precoating water to bring the alcohol content to approximately 52% by volume to again keep the nucleic acids in insoluble form. (Otherwise stated, to prevent solubilization of the nucleic acids.) No wash was used on the rotary precoat filter but the precoating water-alcohol mixture was put through the filter after the paste slurry filtration was completed. The paste slurry remaining in the bed of the precoat filter was pumped to a Nutsche filter to keep the loss of the enzyme to a minimum. Dicalite 4200 was added to assist in the filtration on the Nutsche filter.

The filtrate from both the rotary precoat filter and the Nutsche filter was pumped to a 1000-gallon tank used as storage tank for the supply to a supply tank where 15 gallons of 1.0 molar magnesium sulfate (MgSO$_4$·7H$_2$O) solution and 13 gallons (49.2 liters) of 85% by volume 2-propanol were added. The mixture was supplied to a DeLaval BRPX-207 centrifuge at a rate of 16.6 gallons (62.8 liters) per minute with a 5-minute shoot cycle. When the centrifugation was completed, the bowl was purged by five consecutive 1-second additions of priming water and shoots. The residue comprising the stabilized enzyme concentrate remaining in the bowl and shooting chamber was scrapped off and the bowl and chamber were washed with some of the light phase discharge from the centrifuge. Both the residue and wash went into the stabilized enzyme concentrate product. The product was agitated with a laboratory mixer and put into 1-gallon plastic containers for evaluation and further use to enzymatically convert glucose to fructose.

The overall yield of the stabilized glucose isomerase enzyme concentrate (Batch No. 1) was 11 gallons (41.64 liters) of concentrated liquid containing 109 × 10$^6$ IGIU or about 11,261 IGIU/g. on a dry substance basis. This represented a 63% recovery of the total activity present in the whole cell broth used as the starting material. A more complete analysis of the stabilized enzyme concentrate is provided in Table III.

TABLE III

| Analysis of Stabilized Glucose Isomerase Enzyme Concentrate | |
|---|---|
| | Batch No. 1 |
| Isomerase Activity, IGIU/g, d.s. | 11,261 |
| Specific Activity, IGIU/mg, Protein | 15.1 |
| Dry Substance, % | 22.2 |
| Moisture, Karl Fischer, % | 63.8 |
| Protein, Kjeldahl, % d.b. | 74.7 |
| Ash as Oxide, % d.b. | 11.4 |
| Insoluble/ d.s., % d.b. | 5.3 |
| Mg++, mg/ml | 5.8 |
| Mg+3, molar | 0.24 |
| Mg++/protein ratio | 0.035 |
| 2-Propanol, By difference, % | 14 |

EXAMPLE 2

Several batches of intracellular glucose isomerase enzyme derived from *Streptomyces olivochromogenes* ATCC No. 21,715 were prepared in development stages in the manner described in Example 1(a) using 7.5-liter, 40-liter and 400-liter fermentors for seed development and a 4000-liter fermentor for the final growth stage. Following fermentation, each of the batches containing whole cells of intracellular glucose isomerase enzyme was reduced in temperature from 32° C to 22° C to retard further microbial growth and possible cell autolysis. The batches of broth were then centrifuged to concentrate the cells to form a cell paste. The heavy-phase cell paste was collected in 10-gallon pails, weighed and then pumped to a 1000 gallon digestion tank for cell digestion. To the cell paste there was added, under agitation, a lysozyme enzyme preparation (2X crystalline freeze-dried powder prepared by Miles-Seravac from egg whites having an activity of 23,300 units per milligram of material) to digest the cell walls and release the intracellular glucose isomerase in a soluble form. The lysozyme dosage for each of the batches was 6.8 units per milligram of cell, d.s. The total cell weight on a dry substance basis present in the cell paste was calculated using the final dry cell weight of the whole fermentor broth and the fermentor broth volume. This assumed 100% recovery of the cells on a dry substance basis through the initial concentration step. The lysozyme was added to the cell paste after centrifugation of all the whole broth and before addition of any alcohol to the cell paste. Following the addition of the lysozyme, azeotropic 2-propanol was added to achieve a concentration of 42 ± 1%, by weight. The initial addition of 2-propanol was calculated on the basis of the cell paste weight, less 8% for insolubles, d.s., and the quality of the supply alcohol. Following the adjustment of the alcohol concentration, the pH of the lysate (the cell paste-alcohol slurry) was adjusted to 7.0 with anhydrous monosodium phosphate (to lower the pH). The monosodium phosphate reagent was added in 250-gram increments as required. To prevent localized "hot spots" the reagent was dissolved in water before adding. The lysates were held at a temperature of 28° C to 30° C with turbulent agitation until 100% solubilization of the enzyme occurred. The degree of solubilization was determined by a comparative enzyme analysis of a whole lysate sample and a portion of the same sample from which the cell solids were removed by centrifugations.

At the completion of the digestion period the concentration of the alcohol in the lysates was rechecked and adjusted to within the 42 ± 1% tolerances. The cellular debris was then removed from the lysate using a precoat filter coated with a diatamaceous filter aid (both Dicalite 4200 and Dicalite Speedflow were used as indicated below) slurried up in a 44% to 46% aqueous solution of 2-propanol. An alcohol range slightly above the 42 ± 1% range was used for pre-coating to account for losses in alcohol due to flashing inside the vacuum precoat filter. The digested lysate was filtered as is, i.e., at a pH of 7.0 ± 0.3 and a temperature of 28° to 30°. The filtrates from the precoat filter were routed to a 1000-gallon tank which was used as the supply to the precipitation step.

In four of the batches, the precipitation was done batchwise using a supply tank for the precipitation vessel. The clarified filtrates were batched into the tank (in each run) in approximately 170-gallon volumes. To this was added a 1.0 molar MgSO₄ solution at a dosage of 0.05 gallon (0.189 liter) per gallon (3.785 liter) of clarified lysate and a volume of azeotropic 2-propanol to maintain the over-all level of 2-propanol at about 42%, by weight. During the additions, the solutions were agitated and recycled through a supply pump to facilitate mixing. The precipitated enzyme was held for 10–15 minutes to allow for agglomeration into larger flocs and then recovered by centrifugation using a DeLaval BRPX-207 centrifuge. The solution was supplied to the centrifuge at a rate of 6 to 10 grams/minute and the bowl was shot twice during each batch.

In one batch, (Batch 10) the precipitation was done continuously, using the supply tank as a continuous stirred tank reacter (CSTR). The clarified lysate and MgSO₄ solution were continuously metered into the supply tank through a mixing tee. The 2-propanol concentration of the clarified lysate was adjusted to 44% to 45%, by weight, to compensate for dilution by the MgSO₄ solution, thus maintaining a 42 ± 1% range of alcohol during precipitation. The flow of clarified lysate was controlled using a flow controller. The 1.0 molar MgSO₄ solution was metered in at a rate of 0.05 gallon (0.189 liter) per gallon (3.785 liter) of clarified lysate using a small diaphragm pump. The flow of both solutions was started and a level was built up in the supply tank. The tank was filled to a volume which at the given flow rates of clarified lysate and MgSO₄ gave a 15-minute holdtime. The mixture was then supplied to the centrifuge at a rate equivalent to the flow to the supply tank. The flow rate to the centrifuge was adjusted so as to maintain a constant level in the supply tank. The bowl was given a partial shoot every 10 minutes. The partial shoot was accomplished by reducing the bowl operating water pressure.

Upon completion of the centrifugation of the respective batches, the residual enzyme was removed from the surface of the centrifuge with distilled water and combined with the stabilized enzyme concentrate product. Each of the recovered batches of stabilized enzyme concentrate was agitated until homogenous, bottled and stored at 4° C.

Tables IV and V provide summary of the enzyme recovery efficiencies across the process steps. Table V specifically provides a complete analysis of the stabilized enzyme concentrates.

TABLE IV

Stabilized Enzyme Recovery Analysis

| | Whole Fermentor Broth | | Cell Paste | | Lysate | | Filtrate | |
|---|---|---|---|---|---|---|---|---|
| Batch No. | Volume, liters | Unit Activity, IGIU/g | Wt., kg | Unit Activity, IGIU/g | Wt. kg | Unit Activity, IGIU/g | Volume, liters | Unit Activity, IGIU/ml |
| 6 | 3190 | 15.1 | 584.3 | 75.3 | 1167.2 | 40.8 | 1173.4[b] | 32.4 |
| 7 | 3065 | 18.8 | 578.4 | 79.7 | 1123.2 | 42.8 | 1362.6[b] | 29.2 |
| 8 | 3125 | 18.0 | 602.7 | 84.7 | 1124.8 | 47.3 | 1627.6[c] | 24.6 |
| 9 | 3220 | 18.5 | 658.1 | 89.9 | 1419.2 | 40.4 | 1618.1[c] | 24.9 |
| 10[a] | 3200 | 16.0 | 587.9 | 89.1 | 1105.8 | 42.4 | 1627.6[c] | 18.9 |

[a]Continuous precipitation
[b]Dicalite 4200 filter aid used
[c]Dicalite Speedflow used

TABLE V

Analysis of Stabilized Glucose Isomerase Enzyme Concentrates

| | Batch Nos. | | | | |
|---|---|---|---|---|---|
| | 6 | 7 | 8 | 9 | 10 |
| Isomerase Activity IGIU/g, d.s. | 8,012.5 | 9,089.3 | 9,532.1 | 6,680.6 | 8,963.6 |
| Specific Activity IGIU/mg protein | 12.3 | 14.9 | 14.7 | 13.6 | 15.0 |
| Dry Substance, % | 25.61 | 28.0 | 21.8 | 21.4 | 24.7 |
| Moisture, Karl Fischer, % | 61.9 | 60.9 | 59.4 | 61.4 | 66.2 |
| Protein, Kjeldahl, %, d.b. | 64.9 | 61.0 | 64.8 | 49.4 | 59.9 |
| Ash as oxide, %, d.b. | 37.6 | 13.5 | 13.6 | 35.5 | 13.4 |
| Insoluble, d.s., %, d.b. | 9.7 | 4.6 | 3.7 | 31.6 | 3.3 |
| $Mg^{++}$, mg/ml | 3.8 | 11.6 | 3.3 | 6.73 | 18.6 |
| $Mg^{++}$, molar | 0.16 | 0.48 | 0.14 | 0.28 | 0.77 |
| $Mg^{++}$/Protein Ratio | 0.023 | 0.068 | 0.023 | 0.11 | 0.125 |
| 2-Propanol, % (By Difference) | 12.5 | 11.1 | 18.8 | 17.0 | 9.1 |
| Phosphorous, %, d.b. | — | 2.33 | 1.80 | 8.1 | 2.10 |
| Final Weight of Stabilized Enzyme Concentrate Recovered, | 18,278 | 14,939 | 16,453 | 24,649 | 12,939 |

TABLE V-continued

| Analysis of Stabilized Glucose Isomerase Enzyme Concentrates | | | | |
|---|---|---|---|---|
| Batch Nos. | | | | |
| 6 | 7 | 8 | 9 | 10 | grams, d.s.

EXAMPLE 3

A large batch of intracellular glucose isomerase enzyme derived from Streptomyces olivochromogenes ATCC No. 21,715 was prepared in development stages in the manner described in Example 1(a) using 1-liter, 14 liter, 50 gallon and 1000 gallon fermentors for seed and inoculum development and a 20,000 gallon fermentor for the final growth stage. Upon completion of the fermentation, the broth in the 20,000 gallon fermentor was cooled to about 20° C. It was held without aeration and agitated for short periods of time prior to concentration of the cell solids. The final broth (16,000 gallons or 60,565.6 liters) had an activity of 21.0 IGIU/gram of broth, a peak dry cell yield of 16.5 g/liter and a total activity of 1,270.7 × $10^6$ IGIU. p The whole broth containing the intracellular glucose isomerase was concentrated by centrifuging in a DeLaval BRPX-207 centrifuge to concentrate the cell solids at an on-stream supply rate of approximately 5.0 gallons per minute having a bowl shoot time of 1.75 minutes. The light phase overflow was periodically analyzed and then discarded. The heavy phase cell paste shoots were collected in a receiver can, and then continuously pumped to one of three tanks which were used for digestion. The concentration step resulted in about a 6.4 fold concentration of the cell solids (on a volume basis). The total cell paste recovered amounted to 2,500 gallons (9,463.5 liters) weighing 20,709 pounds (9393.4 kg.) having a total dry substance of 2,431 pounds (1,102.6 kg.). The cell paste was assayed as having 289 pounds (131.09 kg.) of ash 1,433 pounds (649.99 kg.) of protein, 18,278 pounds (8,290.76 kg.) of water, a unit activity of 132 IGIU/g and a total activity, of 1,240.0 × $10^6$ IGIU (98% of the total).

When the volume of the cell paste in a digestor reached 200 gallons (757 liters), 200–230 gallons (757–870.6 liters) of 91.5% 2-propanol were added to the slurry until the digestor tank was filled. After every addition of alcohol, the pH of the resultant slurry in the respective digestor tank was checked and adjusted down to 7.0–7.2, if required with anhydrous monosodium phosphate. Following the intial addition of the alcohol in respective tanks, the lysozyme enzyme was added at increments throughout the balance of the filling period of a dosage of approximately 6.8 units per milligram of cells, on a dry substance basis. The lysozyme used was a 2X crystalline freeze-dried powder prepared by Miles-Seravac from egg whites having a reported activity of 23,000 lysozyme units per milligram of enzyme preparation.

After each tank was filled, final adjustments were made to bring the alcohol concentration of the slurry to within the range of 42 ± 1%, by weight. The lysate (alcohol-cell paste-lysozyme slurry) was constantly agitated as well as recycled through external heat exchangers to maintain temperature control. Tempered water was supplied to the shell side of the heat exchangers to maintain the temperature of the lysate within 28° C to 30° C. The degree of enzyme solubilization was monitored by a comparative enzyme analysis of a whole lysate sample and a portion of the same sample from which the cell solids were removed by centrifugations. When the digestion of a given tank reached about 100% solubilization, the lysate slurry was then ready to be clarified to remove the cellular debris. The digestion times ranged from about 52 to 73 hours, beginning with the filling step. The total lysate slurry from the three digestion tanks had a total volume of 5,138 gallons (19,944.94 liters) weighing 39,590 pounds (17,957.72 kg.) and having a total dry substance of 2,247 pounds (1,019.2 kg.). The lysate slurry was assayed as having 414 pounds (187.78 kg.) of ash, 1,431 pounds (649.09 kg.) of protein, 15,920 pounds (7,221.2 kg.) 2-propanol and 21,423 (9,717.3 kg.) of water. The lysate had a unit activity of 66.6 IGIU/g and a total activity of 1,178.9 × $10^6$ IGIU (which represented 93% of the original total from the fermentation broth).

The lysate slurry was clarified with a precoat filter which was precoated with Dicalite Speedflow (from Grefco Inc.) filter aid to a thickness of 2.25 to 2.5 inches. A total of 600 pounds (272.16 kg.) filter aid was used for the clarification of the lysate slurry. The precoat slurry was made up in a 50% 2-propanol solution at 5% concentration. To conserve the precoat makeup solution, the precoat heel was dropped back to the precoat makeup tank once the precoat was applied. Immediately following dropout of the precoat heel, the digested lysate slurry was brought into the filter. The filtration rates for the clarification step varied from 2.6 gallon/hr,-ft.$^2$ to 3.9 gallon/hr.-ft.$^2$ with an average throughput rate of 2.9 gallon/hr.-ft.$^2$. Following filtration, the clarified filtrate was pumped in 1000 - gallon storage tanks. The cake cuttings from the filter were assayed periodically and discarded. The total lysate had a volume of 4,638 gallons (17,556.7 liters) weighing 35,716 pounds (16,200.5 kg.) and having a total dry substance of 774 pounds (351.08 kg.). The clarified lysate assayed as having 106 pounds (48.08 kg.) of ash, 492 pounds (223.17 kg.) protein, 15,798 pounds (7,165.9 kg.) of 2-propanol and 19,122 pounds (8,673.59 kg.) of water. The unit activity of the clarified lysate was 54.0 IGIU/g and the total activity 875.7 × $10^6$ IGIU (which represented 69% of the original activity from the fermentation broth).

Following the clarification step of the process, the alcohol concentration of the individual tanks of clarified lysate was increased to 44% to 45%, by weight (as determined by specific gravity before processing through the precipitation and stabilization step. Precipitation and stabilization of glucose isomerase enzyme in the clarified lysate solution was carried out by continuously metering the clarified lysate and a 2.0 molar solution of $MgSO_4.7H_2O$ 116 gallons (439.1 liters) (232 pounds of (105.23 kg.) of $MgSO_4$ and 941 pounds (426.8 kg.) of water) through a mixing tee ("T") into a supply tank which was connected to a DeLaval BRPX 207 centrifuge. The 2.0 molar solution of magnesium sulfate was added at a rate of 0.025 gallon per gallon (0.0946 liter per 3.785 liters) of clarified lysate to provide a final solution having a 0.05 molar concentration to $MgSO_4$. The flow of both the $MgSO_4$ solution and clarified lysate solution was started and a level was built up in the supply tank. The tank was filled to a volume which at the given flow rates gave a holdtime of 15 minutes. The mixture was then supplied to the centrifuge at a rate equivalent to the flow to the supply tank. The flow rate to the centrifuge was adjusted to maintain a constant level (and a constant holdtime, e.g., about 15 minutes) in the supply tank.

clarification step. Of this amount, roughly half (about 11.8%) could be accounted for in the filter cake cuttings. The remainder of the losses were attributed to inactivation.

Tables VI and VII provide a summary of the enzyme recovery efficiencies across the process steps. Table VII specifically provides a complete analysis of the stabilized enzyme concentrate.

TABLE VI

| Step of Process | Stabilized Enzyme Concentrate Recovery Analysis (Batch 11) | | |
|---|---|---|---|
| | total Weight, kg. | Unit Activity, as is IGIU/g | Total Activity IGIU |
| Whole Fermentor Broth | 60,454.79 | 21.0 | 1,270.7 × $10^6$ |
| Cell Paste[a] | 9,393.44 | 132.0 | 1,240.0 × $10^6$ |
| Crude Lysate | 17,698.72 | 66.6 | 1,178.9 × $10^6$ |
| Clarified Lysate | 16,200.51 | 54.0 | 875.7 × $10^{6[c]}$ |
| Stabilized Enzyme Concentrate | 287.58 | 11,654[b] | 892.8 × $10^{6[c]}$ |

[a]Represents values obtained by difference or are estimates.
[b]Value is on a dry substance basis.
[c]Total activity of the clarified lysate was determined by estimating the weight of clarified lysate and measuring the isomerase activity therein. Obviously, the actual total weight is higher than amount estimated, since the amount of stabilized enzyme concentrate recovered was more than that determined for the clarified lysate.

The overflow from the centifuge was routed to an 8,000-gallon tank and subsequently processed through a still to recover the 2-propanol for re-use. The stabilized enzyme concentrate was collected in 20-gallon stainless pails and then combined in a 100-gallon agitated vessel. The stabilized enzyme concentrate was mud-like in consistency and medium brown in color. Distilled water was added to the stabilized enzyme concentrate intermittently to resolubilize the enzyme as required (resolubilization was determined visually). When the distilled water was added and the stabilized enzyme concentrate dissolved the color went to a relatively clear coffee black and it had a consistency to that of a light oil.

The recovered stabilized (in resolubilized form) enzyme concentrate had a volume of 73 gallons (276.3 liters) weighing 634 pounds (287.57 kg.) and having a dry substance of 169 pounds (76.66 kg.). The stabilized enzyme concentrate was assayed as having 19 pounds (8.6 kg.) ash, 126 pounds (57.15 kg.) protein, 104 pounds (47.17 kg.) 2-propanol and 360 pounds (163.29 kg.) of water. The stabilized enzyme concentrate had a unit activity of 11,654 IGIU/gram, dry substance basis and a total activity of 892.8 × $10^6$ IGIU (which represents a 70.3% recovery yield of the total activity present in the whole cell broth used as the starting material with the majority of losses (23–24%) occurring at the lysate

TABLE VII

| Analysis of Stabilized Glucose Isomerase Enzyme Concentrate | |
|---|---|
| | Batch No. 11-336 |
| Isomerase Activity, IGIU/g. d.s. | 11,654 |
| Specific Activity, IGIU/mg., Protein | 15.5 |
| Dry Substance, % | 26.6 |
| Moisture, Karl Fischer, % | 56.9 |
| Protein, Kjeldahl, %, d.b. | 75.0 |
| Ash Oxide, % d.b. | 11.3 |
| Insoluble d.s., % d.b. | 0.53 |
| Mg++, mg/m | 5.99 |
| Mg++, molar | 0.25 |
| Mg++/protein ratio | 0.032 |
| 2-Propanol, % (By Difference) | 16.5 |
| Final Weight of Enzyme Recovered, kg., d.s. | 287.58 |

EXAMPLE 4

Several samples of the recovered stabilized glucose isomerase enzyme concentrates form Examples 1–3 and other similar samples of varying activity were subjected to tests to determine their stability on storage at various temperatures. The samples were stored at 4° C, 18° C, 26° C, and 37° C and analyzed for glucose isomerase activity at intervals of 4, 8, and 12 month periods. The following table summarizes the results of this study.

TABLE VIII

| | | Temperature Stability Study of Stabilized Enzyme Concentrates | | | | | | | | | | |
|---|---|---|---|---|---|---|---|---|---|---|---|---|
| | | Percent of Initial Isomerase Activity[a] Temperature | | | | | | | | | | |
| | Initial[a] Activity | 4° C Months | | | 18° C Months | | | 26° C Months | | | 37° C Months | | |
| Batch No. | IGIU/g, d.s. | 4 | 8 | 12 | 4 | 8 | 12 | 4 | 8 | 12 | 4 | 8 | 12 |
| 1 | 10,162 | 101 | 101 | 105 | — | 97 | 98 | 92 | 96 | 96 | 43 | 10 | 6 |
| 2 | 10,289.8 | 100 | 102 | 105 | — | 103 | 107 | 96 | 103 | 106 | 77 | 46 | 40 |
| 3 | 3,910.7[b] | 94 | 100 | 101 | — | 80 | 81 | 76 | 80 | 80 | 39 | 28 | 6 |
| 4 | 2,441.47[b] | 100 | 105 | 102 | 88 | 89 | 82 | 84 | 80 | 61 | 1 | 0 | — |
| 5 | 5,823.7 | 96 | 103 | 107 | — | 91 | 91 | 86 | 90 | 86 | 3 | 1 | 0 |
| 6 | 7,960.9 | 95 | 100 | 105 | — | 99 | 100 | 91 | 98 | 97 | 44 | 5 | 0 |
| 7 | 9,228.57 | 95 | 100 | 107 | — | 98 | 97 | 89 | 96 | 101 | 62 | 23 | 21 |
| 8 | 10,215.59 | 101 | 93 | 82[c] | 85 | 88 | 82 | 83 | 88 | 78 | 5 | 3 | — |
| 9 | 7,504.6 | 100 | 95 | 91 | 88 | 89 | 82 | 83 | 84 | 69 | 5 | 1 | — |
| 10 | 9,113.36 | 90[c] | 96 | 90 | 86 | 87 | 81 | 86 | 86 | 80 | 58 | 48 | 42 |
| 11 | 11,654.0 | 88[c] | 93 | — | 85 | 90 | — | 83 | 88 | — | 33 | 26 | — |

TABLE VIII-continued
Temperature Stability Study of Stabilized Enzyme Concentrates

| Batch No. | Initial[a] Activity IGIU/g, d.s. | Percent of Initial Isomerase Activity[d] Temperature | | | | | | | | | | |
|---|---|---|---|---|---|---|---|---|---|---|---|---|
| | | 4° C Months | | | 18° C Months | | | 26° C Months | | | 37° C Months | | |
| | | 4 | 8 | 12 | 4 | 8 | 12 | 4 | 8 | 12 | 4 | 8 | 12 |
| Average | | 96 | 99 | 100 | 86 | 92 | 90 | 86 | 90 | 85 | 34 | 17 | 13 |

[a]This is the initial assay value at the beginning of this stability study, not the original assay value made following the preparation of the enzyme reported in the previous examples.
[b]These samples had an unusually low initial activity due to faulty processing conditions.
[c]Low values are due to crystallization of proteinaceous material in the enzyme preparation which did not form a part of the total analysis.
[d]The assay of the isomerase activity was accurate to about 10% of the initial isomerase activity which accounts for the values above 100% of the initial activity.

The data in Table VIII is indicative that the stabilized enzyme concentrates of the present invention are capable of retaining greater than 80 ± 10% (and generally greater than 90 ± 10%) of their initial isomerase activity for up to 12 months when stored at 4° and 18° C., and they are capable of retaining up to 80 ± 10% of their initial isomerase activity for up to 8 months when stored at 26° C. Otherwise stated, the stabilized enzyme concentrates exhibited, on an average, less than a 5% loss of their initial isomerase activity when stored at 4° C for 12 months, an average loss of less than about 15% of their initial activity when stored for 12 months at 18° and 26° C.

EXAMPLE 5

A seventeen gallon (64.35 liters) batch of broth containing intracellular glucose isomerase prepared by the procedure described in Example 1(a) was diluted with water and centrifuged to prepare a cell paste. (The seventeen gallon batch of broth came from two 10 gallon fermentor batches having 18.0 IGIU/ml and 16.8 IGIU/ml, respectively. The two fermentor batches were combined for use in preparing the cell paste. The centrifuge cake (cell paste) was placed in a 7.5 liter fermentor jar and diluted with water to attain a total volume of 4.5 liters of slurry. The slurry, which had been stored at 4° C. room temperature for two days was treated with 77 milligrams of lysozyme enzyme preparation (derived from egg whites having about 8,000 lysozyme units per milligrams) and 1930 ml of 2-propanol. The slurry was stirred for 4 hours whereupon an additional 500 milligrams of the lysozyme enzyme preparation was added. The slurry was agitated overnight following temperature adjustment to 20°–30° C (The temperature had increased to about 35°–40° C after the second lysozyme addition which is believed to cause some deactivation of the enzyme). Following digestion, a 500 ml sample of the crude lysate was diluted with 500 ml of water. 123 ml aliquots of the diluted lysate were brought to approximately 50% 2-propanol (on a volume/volume basis) by the addition of 2-propanol. One aliquot of lysate was used as a control. To each aliquot lysate sample, there was added the hereinbelow designated (as setforth in Table IX) amounts of sodium chloride (as a comparison) and magnesium sulfate heptahydrate (MgSO$_4$·7H$_2$O). After the salt addition, as indicated in the Table, the suspensions, including the control were centrifuged and analyzed for glucose isomerase activity and protein content (the latter by the ratio of optical density at 260 and 280 mm (using the Nomograph by E. Adams, distributed by California Corp. for Biochem. Research 3625 Medford St., Los Angeles, 63, California based on the extinction coefficients for enolase and nucleic acids given by Warburg and Christian. Biochem. Z 310, 384 (1942)). The additional details of the experiment and the results of the assay are reported in the following Table.

TABLE IX

| Salt | Weight of Salt, grams | Optical Density at | | | Activity in Supernatant, IGIU/ml |
|---|---|---|---|---|---|
| | | 260nm | 280nm | pH[a] | |
| Control | — | 1.5 | 1.19 | 6.5 | 2.79 |
| NaCl | 1.0 | 1.53 | 1.06 | 6.40 | 3.33 |
| NaCl | 2.0 | 1.55 | 1.08 | 6.38 | 3.14 |
| NaCl | 5.09 | 1.82 | 1.30 | 6.35 | 2.76 |
| MgSO$_4$ | 0.25 | 1.50 | 1.03 | 6.45 | 2.87 |
| MgSO$_4$ | 0.50 | 1.48 | 0.995 | 6.45 | 2.36 |
| MgSO$_4$ | 1.0 | 1.65 | 1.12 | 6.30 | 1.17 |
| MgSO$_4$ | 2.0 | 1.68 | 1.11 | 6.25 | 0.20 |

[a]The pH in these tests was relatively low which could account for the low isomerase activity. However, the pH was not low enough to account for the near complete lack of isomerase activity in the supernatant at the 2.0 gram magnesium sulfate level. It is believed that the temperature increase to 35° – 40° C after the second lysozyme addition caused most of the deactivation of the enzyme activity in this experiment.

The results in Table IX illustrate that the addition of the magnesium sulfate salt to the alcohol-water lysate causes a decrease in the isomerase activity in the supernatant without substantially lowering the nucleic acid content in the supernatant (nucleic acids absorb light at 260 nm). This effect did not occur by the addition of the sodium chloride salt. Thus, the addition of the magnesium sulfate salt to the alcohol-water lysate causes a separation of the glucose isomerase from the soluble nucleic acids. The observed phenomenon was obviously not a typical "salting-out" effect since the level of magnesium sulfate was too low and the result with sodium chloride was the opposite. The sodium chloride experiments did not cause any substantial decrease in isomerase activity in the supernatant.

EXAMPLE 6

To the balance of the 4.5 liter crude lysate (containing solubilized glucose isomerase) from Example 5, there was added filter aid and sufficient 2-propanol to make the slurry 50% with respect to 2-propanol on a volume/volume basis. The slurry was slowly filtered to clarify the solubilized glucose isomerase. A 335 ml sample of the filtrate was analyzed as having 65.2 IGIU/ml. (a total of 21,842 IGIU). To this sample there was added 16.5 ml of 2-propanol and 16.5 ml of a one (1) molar solution of magnesium sulfate heptahydrate (MgSO$_4$·7H$_2$O) at a pH of 8. (Thus, the lysate solution was made 1% with respect to MgSO$_4$, overall, 2% MgSO$_4$ on a water basis). An oily precipitate immediately formed upon the addition of the salt. The solution containing the precipitate was centrifuged and the precipitate was removed. The precipitate was resolubilized with water to a total volume of 10.5 ml. This sample was diluted with water by 402 to 1 and the diluted solution's light transmittance at 260 and 280 nm was 0.284 and 0.350, respectively. From this data the protein content of diluted solution (402 to 1) was determined as 0.33 mg/ml or 133 mg/ml for the 10.5 ml solution. The solution was assayed as having 2040 IGIU/ml. If therefore had a total activity of 21,400 IGIU (98% of the initial activity from the clarified lysate was recovered). The stabilized glucose isomerase enzyme concentrate had a specific activity of 15.3 IGIU/mg of protein. This data in conjunction with the date in Table IX establishes that the magnesium sulfate selectively precipitates and purifies the isomerase enzyme.

EXAMPLE 7

A 67 ml sample of resolubilized alcohol fractionate containing solubilized, cell-free glucose isomerase was stirred with 67 ml of the 2-propanol solution. No precipitate was observed. Thereafter, 2 ml of a one (1) molar solution of magnesium sulfate heptahydrate and 2 ml of the 2-proponal solution were added to the clarified alcohol-water isomerase containing solution. Immediately, a gray-white solid precipitate formed which was subsequently removed and dissolved in water to a volume of 13.0 ml. The stabilized enzyme concentrate was recentrifuged and diluted 101 to 1 with water for the purpose of assaying. The light transmittance of the diluted solution at 260 nm and 280 nm was 0.288 and 0.437 respectively. The protein content of the diluted solution was determined to be 0.46 mg/ml. Thus, the undiluted solution containing the solubilized, stabilized enzyme concentrate had 46.5 mg/ml protein which was assayed as having 482 IGIU/ml and a specific activity of 10.4 IGIU/mg of protein. The total activity in the 13.0 ml stabilized enzyme concentrate was 6,266 IGIU. The centrifugate contained only 150 IGIU.

EXAMPLE 8

A 3,250 ml of a clarified lysate containing solubilized glucose isomerase having 109 IGIU/ml (from the original 4.5 liter batch referred to in Example 5) was mixed with 162 ml of the 2-propanol solution and a 162 ml solution of one (1) molar magnesium sulfate heptahydrate. Immediately an oily precipitate formed which was collected by centrifugation. The precipitate had a volume of 69 ml and it was assayed as having 4,040 IGIU/ml, for a total of 278,760 IGIU. A 1 to 1,000 dilution of a small portion of the stabilized enzyme concentrate was made for the purpose of assay. Its light transmittance at 260 and 280 nm, was observed as 0.315 and 0.345, respectively. The protein content was determined to be 0.299 mg/ml and the specific activity was determined as being 13.5 IGIU/mg of protein. The balance of the stabilized enzyme concentrate was allowed to stand for over 48 hrs. whereupon three (3) layers formed. The three layered slurry was centrifuged and assayed. The top (lipidy) layer of 18.2 ml had 565 IGIU/ml, the center layer of 39 ml had 1,970 IGIU/ml and the bottom layer of 36 ml had 50.80 IGIU/ml. The bottom layer had the lowest light transmittance reading at 260 nm and the highest at 280 nm. The top layer had the highest light transmittance reading at 260 nm.

EXAMPLE 9

A 27.5 gallon batch of broth containing 17.5 IGIU/ml of intracellular glucose isomerase prepared in the manner described in Example 1 (a) was mixed with an equal volume water and centrifuged to a firm cake. The cake was mixed with water to a volume of 26 liters at a pH of 7.45. To this slurry there was added 0.250 grams of lysozyme and 11.5 liters of 2-propanol at a temperature of 27° C. A small amount of antifoam was added and the slurry was stirred. The 37.5 liter water suspension contained 37-44 IGIU/ml. After 20.5 hours, two 8 liter aliquots were removed, whereupon 2-propanol was added in an amount to bring the volume to 50% on a volume/volume basis. Sil-Flo filter aid (3g/g of cells) was added to the slurries which were thereafter filtered and washed with 2 liters of 50% 2-propanol. The filtrate was assayed as having 15 IGIU/ml. An additional one gram of lysozyme was added under agitation to the 21.5 liter balance of the crude lysate to obtain 24.3 IGIU/ml in the filtrate. The enzyme in the filtrate was immediately precipitated by the addition of 1.1 liters of a 1-molar solution of magnesium sulfate and 1.1 liter of 2-propanol to the filtrate. The precipitate containing the stabilized enzyme concentrate was recovered by centrifugation and dissolved in a small amount of water to a volume of 200 ml having about 3,450 IGIU/ml or a total of 690,000 IGIU and a specific activity of about 12.5 IGIU/mg protein.

Two samples from the 200 ml of stabilized enzyme concentrate (one with added propanol parasept as a preservative and one without) were subjected to storage stability test at room temperature (about 26° C.) following re-assay. At the beginning of the storage stability tests, both samples had about 3,300 IGIU/ml. The samples were periodically assayed and at 31 days of storage the sample with the added preservative assayed at 3,165 IGIU/ml and the other sample (no preservative) assayed at 3,140 IGIU/ml. This test is indicative that the stabilized enzyme concentrates of the present invention (with or without preservative) are quite stable on storage and they are capable of retaining up to (or greater) than 95% of their initial activity for more than 30 days when stored at room temperature.

EXAMPLE 10

Comparative Experiments

The purpose of these experiments is to demonstrate the effectiveness of employing various water soluble magnesium salts of the present invention in comparison with other salts known for their ability to precipitate proteins such as ammonium sulfate, sodium sulfate and sodium chloride. Other divalent salts were also employed in this comparison.

A large sample of the lysate (alcohol-water-glucose isomerase solution) from Batch 6 (described in Example 2 and Table IV) was centrifuged in a laboratory centrifuge at 18,000 RPM for 10 minutes prior to use. The alcohol content was determined as being 41.6%, by weight or 49.3% (V/V). To each of several 30 ml samples of the clarified lysates (at room temperature) there was added the hereinafter designated amounts of one (1) molar solution of the salts specified in Table X along with an equivalent volume of 2-propanol. Following salt and alcohol addition, the samples were mixed and then centrifuged at 18,000 RPM for 10 minutes. The supernatants were removed and the precipitates were washed out of the centrifuge tubes and diluted to 25 ml with a cobalt-phosphate buffer ($10^{-3}$ M $Co^{++}$, pH 7.5, 0.05 $MPO_4=$) for assay of glucose isomerase activity and protein determination. The effect of the different salts and concentration on the selective precipitation and purification of the solubilized isomerase enzyme are shown in Table X.

TABLE X
EFFECT OF DIFFERENT SALTS AND CONCENTRATIONS ON THE PRECIPITATION OF ISOMERASE ENZYME

| Salts | Enzyme Recovered | % by Volume of 1 M Salt Added[a] | | | | |
|---|---|---|---|---|---|---|
| | | 1 | 2.5 | 5 | 10 | 20 |
| Magnesium Salts | | | | | | |
| $MgSO_4 \cdot 7H_2O$ | % | 1 | 97 | 100 | 100 | 95 |
| | Sp. Act.[b] | 2.4 | 15.7 | 15.8 | 13.6 | 11.0 |
| $MgCl_2$ | % | 15 | 100 | 103 | 103 | 105 |
| | Sp. Act. | 9.5 | 15.4 | 15.6 | 16.4 | 16.9 |
| $Mg(C_2H_3O_2)$ | % | 3 | 94 | 100 | 99 | 98 |
| | Sp. Act. | 3.7 | 15.1 | 15.4 | 15.3 | 15.9 |
| Monovalent Cation Salts | | | | | | |
| $Na_2SO_4$ | % | 0 | 0 | 0 | 1 | 16 |
| | Sp. Act. | 0 | 0 | 0 | 2.6 | 8.4 |
| $(NH_4)_2SO_4$ | % | 0 | 0 | 0 | 1 | 1 |
| | Sp. Act. | 0 | 0 | 0 | 2.6 | 2.9 |
| NaCl | % | 0 | 0 | 0 | 1 | 1 |
| | Sp. Act. | 0 | 0 | 0 | 1.8 | 1.9 |
| Other Divalent Cation Salts | | | | | | |
| $BaCl_2$ | % | — | 93 | 76 | 18 | — |
| | Sp. Act. | — | 11.9 | 8.8 | 8.4 | — |
| $SrCl_2$ | % | — | 104 | 94 | 28 | — |
| | Sp. Act. | — | 14.3 | 12.7 | 12.7 | — |
| $CaCl_2$ | % | — | 65 | 57 | 19 | — |
| | Sp. Act. | — | 8.9 | 7.9 | 6.2 | — |
| $CoCl_2$ | % | — | 61 | 18 | 1 | — |
| | Sp. Act. | — | 9.1 | 5.6 | 0.8 | — |
| $MnCl_2$ | % | — | 21 | 29 | 8 | — |
| | Sp. Act. | — | 2.8 | 3.9 | 2.6 | — |

[a]Respective Molar concentrations are 0.01, 0.025, 0.048, 0.09, and 0.17.
[b]Protein for specific activity (Sp. Act.) determined by optical density at 280/260 nm, and reported as IGIU/mg of protein.

The results shown in Table X demonstrate that sodium sulfate and ammonium sulfate do not precipitate the glucose isomerase enzyme from the lysate as effectively and at as low a concentration as the magnesium salts. Ammonium sulfate did not precipitate any enzyme and sodium sulfate provided only a 19% recovery of the glucose isomerase enzyme. This recovery (however small) was not necessarily due to precipitation but may be attributable to a phase separation (an alcohol-water and a salt-water phase). The protein is more soluble in the salt-water phase than the alcohol-water phase. The salt-water phase non-specifically extracts proteins from the alcohol-water phase. Since the salt-water phase is more dense, it is collected as product. Also, the other monovalent salt tested, sodium chloride, did not precipitate the glucose isomerase enzyme.

Divalent salts other than the magnesium salts precipitated the glucose isomerase enzyme but the recoveries and purities were not equivalent to those obtained with the magnesium salts. Barium and strontium salts performed the best of the non-magnesium salts tested, but these salts are not desirable from a food use standpoint.

Of the salts tested, only the magnesium salts precipitated the enzyme efficiently with high specific activity. The magnesium salt concentration used is a small fraction of that required to precipitate proteins from an aqueous solution using classical salting-out techniques, i.e., using ammonium and sodium sulfates. In fact, the phenomenon is contrary to the reported literature (e.g., *Advances in Protein Chemistry*, Volume XI, pages 416–418 [1956] and *Advances in Protein Chemistry*, Volume 16, page 216 [1961]), the latter citation of which indicates that magnesium sulfate is less effective than sodium sulfate or ammonium sulfate in the salting-out of proteins.

Also evident from the data in Table X is that at increasing concentrations of magnesium sulfate (above 0.08 molar), the specific activity decreases, indicating a more indiscriminate precipitation of protein with the glucose isomerase enzyme. It was observed that phase separation occurred with the magnesium sulfate. The decrease in specific activity follows the apparent increased solubility of protein in the salt-water phase. With magnesium chloride and magnesium acetate, no phase separation occurred and the specific activities remained constant, if not increasing as in the case of magnesium chloride.

IMMOBILIZATION OF SOLUBLE GLUCOSE ISOMERASE

EXAMPLE 11

In this example, it will be demonstrated that the highly purified and stabilized enzyme concentrate of the present invention is capable of producing an immobilized glucose isomerase having a higher binding capacity than normally solubilized glucose isomerase.

The solubilized glucose isomerase was prepared from whole cells containing intracellular glucose isomerase prepared in the manner described in Example 1 (a). To aid in the recovery of the whole cells, Sil-Flo filter aid and $Mg(OH)_2$ were added to the broth and the mixture was then washed with 2-propanol, dried and ground in a Wiley mill. During extraction of the glucose isomerase from the cells, the mixture containing the cells was treated with $MgSO_4 \cdot 7H_2O$ in an amount sufficient to make the slurry 0.01 molar with respect to the magnesium salt and adjusted to a pH of 8.0 with 0.1 molar KOH. The crude glucose isomerase enzyme was extracted from a 6.5 gram sample (as is basis) of dry cell preparation with 50 ml of extractant. The mixture was stirred for 45 minutes at room temperature and then centrifuged at 4° C. An extract of 42 ml was obtained containing 26–27 IGIU/ml. The glucose isomerase enzyme solution prepared by this technique and the stabilized enzyme concentrate of the present invention (prepared in accordance with Example 1 [b]) were sorbed onto a variety of water insoluble carriers using the following procedure.

In a 150-ml beaker, 2 g. (dry basis) of the water insoluble carrier was mixed with 30 ml of a solution containing 0.1 molar MgSO$_4$·7H$_2$O and adjusted to a pH 8.0 with KOH. To this mixture there was added sufficient isomerase liquid (either the normally solubilized or the enzyme concentrate of the present invention) to contact the carrier with 1,000–3,000 IGIU of the isomerase (depending on the capacity of the carrier). Thereafter, additional 0.01 molar MgSO$_4$·7H$_2$O solution was added to provide a liquid volume of 50 ml. The mixture containing enzyme and water insoluble carrier was then thoroughly mixed by stirring for 30 minutes, filtered and washed with the 0.01 molar MgSO$_4$·7H$_2$O solution. The combined filtrate and washings were transferred to a 250 ml volumetric flask, diluted to volume with the 0.01 molar MgSO$_4$·7H$_2$O solution and assayed against the original soluble isomerase enzyme preparation for isomerase activity using a Technician Auto Analyzer.

The "binding capacity" ("BC") for the respective water insoluble carriers was calculated by difference using the following formula:

$$\text{"BC" IGIU/g. d.b.} = \frac{\text{Total IGIU Present - Total IGIU in Filtrate and Washings}}{\text{g. Carrier, d.b.}}$$

Table XI summarizes the results of this experiment which compares the binding capacity with various carriers of normally solubilized glucose isomerase with the stabilized enzyme concentrate of the present invention.

TABLE XI

Binding Capacity for Various Carriers Using Solubilized Glucose Isomerase

| Carrier Anion Exchange Resins | Carrier Preconditioning | Isomerase[a] Used | Binding Capacity IGIU/g./d.b. |
|---|---|---|---|
| Amberlite IRA-938 | Buffer[b] | N | 152 |
| Amberlite IRA-938 | Buffer[c] | SEC | 333 |
| Amberlite IRA-93 | Buffer[b] | N | 37 |
| Amberlite IRA-93 | Buffer[c] | SEC | 113 |
| DEAE Cellulose | | | |
| Selectacel - Type 20 | MgSO$_4$[c] | N | 851 |
| Selectacel - Type 20 | Buffer[b] | SEC | 1487 |
| Selectacel - Type 40 | MgSO$_4$[d] | N | 936 |

[a]N = normal soluble glucose isomerase; SEC = Stabilized Enzyme Concentrate of the invention
[b]Buffer solution containing 0.05 M pH 7.5 potassium phosphate buffer, 0.01 M MgSO$_4$·H$_2$O and 0.001 M Co(cl$_2$·6H$_2$O.
[c]Tris Buffer (0.05M, pH 7.5) containing 0.01 M MgSO$_4$·7H$_2$O.
[d]0.01 M MgSO$_4$·7H$_2$O adjusted to pH 8.0 with 0.1 N KOH.

The data in Table XI shows that the binding capacity of DEAE cellulose is nearly two times greater for the stabilized enzyme concentrate than for the normally solubilized enzyme and in the case of synthetic anion exchange resins, 2–3 times greater. It was found during the course of these experiments that the binding capacity of DEAE cellulose for the stabilized enzyme concentrate is substantially increased by preconditioning the carrier at a lower pH level. For example, at a pH level of 6.5, the carrier binds 3120 IGIU/g. whereas, the untreated carrier binds only 1634 IGIU/g. Using the stabilized enzyme concentrate of the present invention it was possible to bind 10.9 million IGIU per cubic foot on the Type 20 DEAE cellulose. This biocatalyst could then be used to convert glucose to high fructose corn syrup by continuously passing a glucose solution through the biocatalyst which could be placed in columns or in pressure leaf filter elements.

Also seen from Table XI, the maximum binding capacity attained using normally solubilized glucose isomerase was 936 IGIU/g. with Type 40 Selectacel which had an exchange capacity of 0.89 meq./g. Although Type 20 Selectacel, which had an exchange capacity of 0.87 meq./g. had a slightly lower binding capacity than Type 40, the Type 20 is more practical for commercial use because it has a larger particle size and, therefore, exhibits better flow rates.

EXAMPLE 12

In the following experiments, the stabilized enzyme concentrate of the present invention was immobilized onto a number of water insoluble carriers and tested for use in the continuous enzymatic conversions of glucose to high fructose corn syrup. Continuous conversions using immobilized whole cells were also conducted. In each of the conversions, except where indicated in Table XII, a jacketed 1.5 × 8-cm column was used.

The columns were prepared by placing a glass wool pad at the base of the column and partially filling the column with water. In the case of using the water insoluble carriers, the water insoluble carriers were added to the columns and topped with a glass wool pad. The stabilized enzyme concentrate of the present invention (Batch 1, Example 1 [b]) was then slowly passed through the column followed by washing with a small amount of distilled water. The washings and column effluent were combined and assayed for glucose isomerase activity. The amount of enzyme sorbed was determined by difference.

In the case of the immobilized whole cells (the product of Example 1 [a] containing the Sil-Flo filter aid), 5 g. of the whole cell enzyme preparation with and without 100 mg. of Mg(OH)$_2$ was added to the columns respectively. The columns were topped with a glass wool pad.

The continuous conversions were conducted by continuously feeding the columns with 50% w/w redissolved crystalline dextrose (600g/liter of solution) containing 0.004–0.0055 molar magnesium sulfate having a pH of 8.4–8.6. The columns were equilibrated when necessary and the continuous enzymatic isomerization was conducted at 60° C. by pumping 60° C. water through the jacket of the columns. The flow of the feed through the columns was maintained by the combination of vacuum at the base of the column and nitrogen gas on the feed. The flow rate was regulated by varying the gas pressure on the feed.

The apparent enzyme activity, "KE", was determined using the equation:

$$KE = BVH \times \log\left[\frac{\%Le}{\%Le - \%L}\right]$$

where:
BVH = column flow rate in bed volumes/hr.
%Le = dextrose-fructose equilibrium value which at 60° C. is 51.2
%L = % ketose of the column effluent
The bed volumes/hr. at 45% levulose, $BVH_{45}$ = KE/0.916

The half-life, the time required for half of the apparent activity of the column to be lost, was determined by taking samples during two or more weeks of column operation and measuring the KE. The half-life was obtained from the slope of the line, determined by least squares method, of the plot of lnKE vs time. This method assumes that the enzyme decay rate is first order. The initial bed volumes/hr. at 45% ketose, $BVH_{45'}$, was determined from the intercept of the least square line.

The efficiency, "Eff", was determined by using the equation:

$$Eff = BVH_{45'\,c}/MM\ IGIU/ft^3$$

The results of these continuous conversions are set forth in Table XII.

TABLE XIII

Effect of Enzyme Loading Upon Continuous Conversions[1]

| IGIU Offered MM IGIU/ft³ | IGIU Sorbed MM IGIU/ft³ | % of Enzyme Sorbed | Efficiency | Half-Life (Days) |
|---|---|---|---|---|
| 14.2 | 13.9 | 98 | 0.5 | 66 |
| 20.2 | 18.4 | 91 | 0.45 | 67 |
| 26.3 | 19.6 | 75 | 0.43 | 60+ |

[1]The controlled pore alumina carrier was comprised of 97-98%, d.b. $Al_2O_3$ and 2-2.4% d.b. MgO having a surface area of 80 m²/g as described in U.S. Ser. No. 507,209.

The stabilized enzyme concentrate of the present invention efficiently sorbs onto the controlled pore alumina carrier to provide a biocatalyst that is feasible for continuously converting glucose to high fructose corn syrups. The high binding efficiencies and long half-lives render this biocatalyst suitable for commercialization on a large scale.

EXAMPLE 13

While the earlier examples demonstrate the use of 2-propanol as the water miscible organic solvent in preparing the stabilized enzyme concentrates, other water miscible organic solvents may be used in accordance with the practice of the present invention. The following experiment was conducted to demonstrate the use of water miscible organic solvents other than 2-propanol.

An intracellular glucose isomerase enzyme broth

TABLE XII

CONTINUOUS CONVERSION RESULTS USING DIFFERENT IMMOBILIZED GLUCOSE ISOMERASE ENZYME PREPARATIONS

| Continuous Conversion System | Average Loading MM IGIU/ft³ | Efficiency | Half-Life(days) | IGIU/g.d.s. at 2 Half-Lines |
|---|---|---|---|---|
| Controlled Pore Alumina[1] | 14.1 | 0.61 | 48 | 0.09 |
| Basic Magnesium Carbonate | 1.95 | 0.29 | 36 | 0.26 |
| DEAE Rice[2] | 3.22 | 0.57 | 14 | 0.35 |
| DEAE Cellulose (Selectacel-20) | 8.91 | 0.51 | 12 | 0.42 |
| DEAE Starch | 1.00 | 0.39 | 11.2 | 0.60 |
| DEAE Wood Chips[2] | 10.5 | 0.22 | 18.3 | 0.65 |
| Darco S-51 Carbon | 0.16 | 0.22 | 5.6 | 2.12 |
| Amberlite IRA - 904 | 6.45 | 0.49 | 37.0 | 0.15 |
| Amberlite IRA - 937 | 0.39 | 1.13 | 4.3 | 0.54 |
| Sil-Flo Cells (no Mg(OH)₂) | 1.92 | 0.49 | 14 | 0.38 |
| Sil-Flo Cells + Mg(OH)₂ | 2.21 | 0.44 | 17 | 0.36 |

[1]Controlled Pore Alumina as described in U.S. Pat. Nos. 3,850,751 and 3,868,304 and U.S. Ser. No. 507,209, filed September 18, 1974 (Eaton and Messing), was placed in jacketed 3.0 × 18 cm column first filled with 3 mm of glass beads then topped with a fine mesh screen. The column was then partially filled with 0.1 M magnesium acetate solution. 55.6 g. of carrier was added to the column which was then backwashed with the 0.1 M magnesium acetate solution to fluidize the bed. A fine mesh screen was placed on top of the carrier and topped with glass beads. The column was then fed with 40,000 – 45,000 IGIU of the stabilized enzyme concentrate and washed with the magnesium acetate solution.

[2]A jacketed column 3.0 × 18 cm prepared in the manner of Footnote 1 was used except that a magnesium sulfate solution was used in place of magnesium acetate. The enzyme was sorbed on the carrier prior to filling the column by first treating 38 g. of DEAE Rice or DEAE wood chips with HCL, washing with water and thereafter suspending the DEAE Rice in 750 ml of 0.1 M MgSO₄ containing 8 ml of the stabilized enzyme concentrate (Batch 1).

The data in Table XII demonstrates that the stabilized enzyme concentrate of the present invention can be efficiently sorbed onto a plurality of water insoluble carriers and used to continuously convert glucose to high fructose corn syrups. The best enzyme utilization obtained was obtained sorbing the stabilized enzyme concentrate onto the controlled pore alumina carrier. The high enzyme utilization obtained is the result of the high efficiency and long half-life. The basic magnesium carbonate and the synthetic anion exchange resin, Amberlite IRA-904, carriers in combination with the stabilized enzyme concentrate of the present invention also produced good results in the continuous conversion experiments.

The procedure described above with respect to the controlled pore alumina carrier was repeated using the stabilized enzyme concentrate of Example 3. Table XIII summarizes the results of this experiment.

having 18.1 IGIU/g of broth was prepared in the manner described in Example 1 (a). This broth was filtered to obtain a cell paste having 120 IGIU/g. The cell paste was treated with a lysozyme enzyme preparation to digest the cell walls of the intracellular glucose isomerase. The solubles of this lysate had 123 IGIU/g. of isomerase activity. The lysate was diluted with sufficient water so that the isomerase activity of the lysate was 110 IGIU/ml. To 50-ml aliquots of this lysate there was slowly added the water miscible organic solvents as indicated below. The amount of solvent was added up to the point where the isomerase protein just begins to precipitate. The solvent/lysate mixture was stirred for 5–10 minutes and thereafter the insoluble material including cellular debris and nucleic acids were removed by centrifugation. To 20 ml aliquots of each of the supernatants there was added under agitation 1 ml of 1 M MgSO₄·7 H₂O (5% by volume) and sufficient solvent to compensate for the dilution of solvent in the supernatant caused by the MgSO$_4$·7 H$_2$O addition. The aqueous mixtures containing the cell-free glucose isomerase enzyme, water miscible organic solvent and MgSO$_4$·7 H$_2$O were allowed to stand for about 15 minutes with intermittent stirring. The mixtures were centrifuged whereupon the precipitated stabilized enzyme concentrates were recovered. The results of this experiment are set forth in Table XIV.

TABLE XIV

| Solvent | Volume of Solvent[c] Added per Volume of Lysate | % IGUI Recovered | Specific Activity[a] IGIU/mg of Protein |
|---|---|---|---|
| 2-Propanol | 1 | 100 | 11.8 |
| Acetone | 0.8 | 92 | 10.0 |
| Methanol | 2.4 | 87 | 12.0 |
| Ethanol | 1.3 | 98 | 11.6 |
| 1-Propanol | 0.8 | 82 | 10.5 |
| t-Butanol | 0.65 | 95 | 6.4 |
| p-Dioxane[b] | 0.7 | 25 | 5.7 |

[a]Protein for specific activity determined by optical density of 280/260 mm.
[b]10% by volume 1 M MgSO$_4$ used to effect precipitation, all other precipitations effected with 5% by volume 1 M MgSO$_4$.
[c]Lysate had a specific activity of approximately 2 IGIU/mg of protein.

It can be seen from the above data that a variety of water miscible organic solvents can be effectively used in the practice of the invention. The alcohols and ketones having up to 3 carbon atoms, which constitute a preferred embodiment of the invention, were the most effective solvents in selectively recovering the isomerase enzyme. It is also apparent from the data that the lower molecular weight solvents require more solvent to effectively recover the isomerase. For example, the amount of methanol needed for selective recovery is 2.4 volumes (approximately 67%, by weight) as compared with 1 volume of 2-propanol (42%, by weight) per volume of lysate.

It will be understood by those skilled in the art that various modifications of the present invention as described in the foregoing examples may be employed without departing from the scope of the invention. Many variations and modifications thereof will be apparent to those skilled in the art and can be made without departing from the spirit and scope of the invention herein described.

What is claimed is:

1. A process for preparing a stabilized glucose isomerase enzyme concentrate, comprising:
   a. treating an aqueous slurry of microbial cells containing intracellular glucose isomerase to release the isomerase from the cells and to thereby obtain a soluble cell-free glucose isomerase enzyme and insoluble materials in the resulting aqueous slurry;
   b. treating the resulting aqueous slurry with a water miscible organic solvent selected from the group consisting of methanol, ethanol, propanol, 2-propanol, t-butanol, acetone and p-dioxane in an amount from about 30% to about 60% on a weight percent basis to precipitate a substantial portion of the non-isomerase proteinaceous materials and nucleic acids from said aqueous slurry upon release of the isomerase from the cells, but insufficient to precipitate the isomerase enzyme; said water miscible organic solvent being characterized as capable of decreasing the solubility of non-isomerase proteins and nucleic acids in aqueous media;
   c. removing the insoluble materials including cellular debris and nucleic acids from said aqueous slurry to provide an aqueous mixture containing cell-free glucose isomerase enzyme and water miscible organic solvent;
   d. treating said aqueous mixture containing a cell-free glucose isomerase enzyme and the water miscible organic solvent with a substantially water soluble magnesium salt selected from the group consisting of magnesium acetate, magnesium chloride and magnesium sulfate in an amount sufficient to provide said mixture from about 0.02 molar to about 0.3 molar with respect to the magnesium salt based on the total volume of the mixture to precipitate and to provide a stabilized enzyme concentrate comprising an enzyme magnesium precipitate in the mixture; and
   e. recovering the stabilized enzyme concentrate comprising glucose isomerase enzyme, magnesium in an amount ranging from about 0.1 to about 2 molar measured as Mg$^{++}$, water and water miscible organic solvent.

2. The process of claim 1, wherein the water miscible organic solvent is 2-propanol.

3. The process of claim 1, wherein the substantially water soluble magnesium salt is magnesium sulfate.

4. The process of claim 1, wherein the substantially water soluble magnesium salt is magnesium chloride.

5. The process of claim 1, wherein the recovered stabilized enzyme concentrate is characterized as having an isomerase activity of at least about 5,000 IGIU/gram, dry basis and a specific isomerase activity of at least about 10 IGIU/mg of protein.

6. The process of claim 1, wherein the recovered stabilized enzyme concentrate is characterized as having an isomerase activity of at least about 8,000 IGIU/gram, dry basis and a specific isomerase activity of at least about 12 IGIU/mg of protein.

7. The process of claim 1, wherein the aqueous mixture containing the cell-free glucose isomerase enzyme and water miscible organic solvent is prepared by:
   a. treating the aqueous slurry of cells containing intracellular glucose isomerase with a water miscible organic solvent and a lysozyme enzyme preparation;
   b. allowing the cellular material to digest by the action of the lysozyme enzyme to provide insoluble materials comprising cellular debris, nucleic acids and soluble materials comprising cell-free glucose isomerase enzyme, water miscible organic solvent and water;
   c. removing the insoluble materials; and
   d. recovering therefrom an aqueous mixture containing cell-free glucose isomerase and water miscible organic solvent.

8. The process of claim 1, wherein the glucose isomerase enzyme is derived from a microrganism of the *Streptomyces genus.*

9. The process of claim 1, wherein the glucose isomerase enzyme is derived from a microorganism which is a member selected from the group consisting of *Streptomyces olivochromogenes* ATCC No. 21,713, ATCC No. 21,714; ATCC No. 21,715, variants and sub-mutants thereof.

10. The process for preparing a stabilized glucose isomerase enzyme concentrate, comprising:
   a. mixing an aqueous slurry comprising cells containing an intracellular glucose isomerase enzyme derived from a microorganism which is a member selected from the group consisting of *Streptomyces olivochromogenes* ATCC No. 21,713, ATCC No.

21,714, ATCC No. 21,715, variants and sub-mutants thereof with 2-propanol in an amount sufficient to provide the aqueous slurry from about 40 to about 45 weight percent with respect to 2-propanol;

b. digesting the cells in the 2-propanol-water slurry with a lysozyme enzyme preparation to thereby form a soluble cell-free glucose isomerase enzyme in the 2-propanol-water slurry, and insoluble materials comprising cellular debris and nucleic acids.

c. removing the insoluble materials and recovering an aqueous mixture containing a solution of cell-free glucose isomerase enzyme, 2-propanol and water;

d. treating said aqueous mixture containing the cell-free glucose isomerase enzyme and 2-propanol with magnesium sulfate heptahydrate in an amount sufficient to provide the aqueous mixture about 0.05 molar with respect to magnesium sulfate heptahydrate to form a stabilized glucose isomerase enzyme concentrate comprising an enzyme-magnesium precipitate containing concentrated cell-free glucose isomerase enzyme, 2-propanol, water and magnesium; and e. recovering a stabilized glucose isomerase enzyme concentrate comprising glucose isomerase enzyme, magnesium in an amount ranging from about 0.1 to about 2 molar with respect to $Mg^{++}$, water and 2-propanol.

11. The process of claim 10, wherein the recovered stabilized enzyme concentrate of Step (e) is diluted with a small amount of water.

12. The process of claim 10, wherein 2-propanol is added, as needed in Steps (a), (b), (c) and (d) to maintain the concentration at about 42±1%, weight percent with respect to 2-propanol.

13. The process of claim 10, wherein the recovered stabilized enzyme concentrate is characterized as having an isomerase activity of at least about 8,000 IGIU/gram, dry basis and a specific isomerase activity of at least about 12 IGIU/mg protein.

14. The process of claim 1 wherein the recovered stabilized enzyme concentrate is dried to a solid product.

15. The process of claim 10 wherein the recovered stabilized enzyme concentrate is dried to a solid product.

16. A process for purifying an intracellular glucose isomerase enzyme, comprising:

a. mixing an aqueous mixture comprising cells containing intracellular glucose isomerase derived from a microorganism of the *Streptomyces genus* with 2-propanol in an amount sufficient to provide the aqueous mixture from about 40 to about 45 weight percent with respect to 2-propanol and obtain an aqueous slurry of 2-propanol and said cells;

b. digesting the cells containing the intracellular glucose isomerase with a lysozyme enzyme preparation to thereby release a soluble cell-free glucose isomerase enzyme into the aqueous 2-propanol slurry and precipitate insoluble materials comprising cellular debris and nucleic acids;

c. removing the insoluble materials including cellular debris and nucleic acids from said aqueous slurry to provide an aqueous mixture containing cell-free glucose isomerase enzyme and 2-propanol;

d. treating said aqueous mixture with a substantially water soluble magnesium salt selected from the group consisting of magnesium acetate, magnesium chloride and magnesium sulfate to precipitate a stabilized enzyme concentrate; and e. recovering the stabilized enzyme concentrate comprising glucose isomerase enzyme, magnesium in an amount ranging from about 0.1 to about 2 molar measured as $Mg^{++}$, water and 2-propanol.

17. The process of claim 16, wherein the 2-propanol is added, as needed in Steps (a), (b) and (c) to maintain the concentration at about 42±1, weight percent with respect to 2-propanol.

18. The process of claim 16, wherein the lysozyme enzyme preparation is added prior to the alcohol addition.

19. A stabilized glucose isomerase enzyme concentrate derived from a microorganism of the genus *Streptomyces* and prepared by the process of claim 1 comprising an enzyme concentrate of (1) a cell-free glucose isomerase enzyme which is substantially free of nucleic acids, (2) $Mg^{++}$, and (3) 2-propanol in an amount ranging from about 5 to about 25% by weight, said enzyme concentrate being characterized as having:

a. a protein content ranging from about 5 to about 80% by weight, dry basis:

b. a $Mg^{++}$ content ranging from about 3 to about 45 mg. of $Mg^{++}$ per ml. of enzyme concentrate;

c. a $Mg^{++}$/protein ratio ranging from about 0.02 to about 0.75;

d. a specific isomerase activity of at least about 10 IGIU/mg of protein; and e. a stability such that it is capable of retaining up to 95% of its initial isomerase activity when stored at 26° C for up to 30 days.

20. The enzyme concentrate of claim 19, wherein the protein content is in the range from about 60 to about 75% by weight, dry basis.

21. The enzyme concentrate of claim 19, wherein the $Mg^{++}$/protein ratio ranges from about 0.03 to about 0.5 and the $Mg^{++}$ content ranges from about 5 to about 25 mg. of $Mg^{++}$ per ml. of enzyme concentrate.

22. The enzyme concentrate of claim 19, wherein the enzyme concentrate has a moisture content ranging from about 50 to about 80% and a dry substance content ranging from about 5 to about 30%, by weight.

23. The enzyme concentrate of claim 19, wherein the enzyme concentrate is further characterized as having at least 5,000 IGIU/gram, dry basis.

24. The enzyme concentrate of claim 19, wherein the enzyme concentrate is further characterized as having at least 8,000 IGIU/gram dry basis and a specific isomerase activity of at least about 12 IGIU/mg. of protein, and a stability such that it retains at least about 80±10% of its initial isomerase activity when stored at 18° C for up to one (1) year.

25. The enzyme concentrate of claim 19, wherein the glucose isomerase is derived from a microorganism which is a member selected from the group consisting of *Streptomyces olivochromogenes* ATCC No. 21,713, ATCC No. 21,714, ATCC No. 21,715, variants and sub-mutants thereof.

26. The enzyme concentrate of claim 19, which is further characterized as being free from added cobalt.

27. A liquid and substantially water soluble stabilized glucose isomerase enzyme concentrate comprising an enzyme concentrate of (1) a cell-free glucose isomerase which is substantially free of nucleic acids derived from a microorganism which is a member selected from the group consisting of *Streptomyces olivochromogenes*

ATCC No. 21,713, ATCC No. 21,714, ATCC No. 21,715, variants and sub-mutants thereof, and (2) $Mg^{++}$ derived from a salt selected from the group consisting of magnesium acetate, magnesium chloride and magnesium sulfate, said enzyme concentrate being characterized as having:

a. a protein content ranging from about 60 to about 75% by weight, dry basis;
b. a $Mg^{++}$ content ranging from about 5 to about 18 mg. of $Mg^{++}$ per ml. of enzyme concentrate;
c. a $Mg^{++}$/protein ratio ranging from about 0.03 to about 0.5;
d. a specific isomerase activity of at least about 12 IGIU/mg. of protein;
e. a 2-propanol content ranging from about 20 to about 30% by weight;
f. a moisture content ranging from about 55 to about 70% by weight;
g. a total isomerase activity of at least about 8,000 IGIU/gram, dry basis; and
h. a stability such that it is capable of retaining up to about 95% of its initial isomerase activity when stored at 26° C for up to 30 days and up to 80±10% of its initial isomerase activity when stored at 18° C for up to 12 months.

* * * * *

UNITED STATES PATENT OFFICE
CERTIFICATE OF CORRECTION

PATENT NO. : 4,077,842
DATED : March 7, 1978
INVENTOR(S) : Robert Paul Cory, deceased It is certified that error appears in the above-identified patent and that said Letters Patent are hereby corrected as shown below:

On the Title Page, insert as "[73]" the following --
Assignee: CPC INTERNATIONAL, INC., Englewood Cliffs, New Jersey --.

Signed and Sealed this

Nineteenth Day of September 1978

[SEAL]

Attest:

RUTH C. MASON
*Attesting Officer*

DONALD W. BANNER
*Commissioner of Patents and Trademarks*

UNITED STATES PATENT AND TRADEMARK OFFICE
CERTIFICATE OF CORRECTION

PATENT NO. : 4,077,842
DATED : March 7, 1978
INVENTOR(S) : Robert Paul Cory

It is certified that error appears in the above–identified patent and that said Letters Patent are hereby corrected as shown below:

Column 3, line 20, "chromotography" should read --chromatography--.
Column 3, line 65, "porous" should read --pore--.
Column 14, line 2, "scrapped" should read --scraped--.
Column 14, line 27, "Insoluble/d.s." should read --Insoluble d.s.--
Column 14, line 29, "$Mg^{+3}$" should read --$Mg^{++}$--.
Column 15, line 18, "diatamaceous" should read --diatomaceous--.
Column 16, line 8, "reacter" should read --reactor--.
Column 17, line 42, "digestor" should read --digester--.
Column 17, line 45, "digestor" should read --digester--.
Column 17, line 47, "digestor" should read --digester--.
Column 17, line 49, "intial" should read --initial--.
Column 19, line 25, "centifuge" should read --centrifuge--.
Column 21, line 59, "setforth" should read --set forth--.
Column 23, line 58, "lipidy" should read --lipid--.
Column 29, line 20, "$BVH_{45°}$" should read --$BVH_{45}$--.
Column 29, line 25, "$BVH_{45°C}$" should read --$BVH_{45}$--.
Column 30, line 34, "Half-Lines" should read --Half-Lives--.
Column 32, line 54, "microrganism" should read --microorganism--.
Column 34, line 23, "5" should read --50--.

Signed and Sealed this

Nineteenth Day of June 1979

[SEAL]

Attest:

RUTH C. MASON
Attesting Officer

DONALD W. BANNER
Commissioner of Patents and Trademarks